(12) United States Patent
Piwowarski et al.

(10) Patent No.: US 12,329,738 B2
(45) Date of Patent: Jun. 17, 2025

(54) UROLITHIN A AND A COMPOSITION CONTAINING SAME FOR EXTERNAL USE IN INFLAMMATIONS OF VARIOUS ETIOLOGIES

(71) Applicant: WARSZAWSKI UNIWERSYTET MEDYCZNY, Warsaw (PL)

(72) Inventors: Jakub Piwowarski, Umer (PL); Sebastian Granica, Warsaw (PL); Mariusz Sacharczuk, Warsaw (PL); Marek Naruszewicz, Zalesie Gome (PL)

(73) Assignee: MICROBIOTA MED. SP. Z O.O., Warsaw (PL)

( * ) Notice: Subject to any disclaimer, the term of this patent is extended or adjusted under 35 U.S.C. 154(b) by 932 days.

(21) Appl. No.: 17/298,756

(22) PCT Filed: Nov. 29, 2019

(86) PCT No.: PCT/IB2019/060337
§ 371 (c)(1),
(2) Date: Jun. 1, 2021

(87) PCT Pub. No.: WO2020/110089
PCT Pub. Date: Jun. 4, 2020

(65) Prior Publication Data
US 2022/0062226 A1    Mar. 3, 2022

(30) Foreign Application Priority Data

Nov. 29, 2018  (PL) .......................................... 427944

(51) Int. Cl.
*A61K 31/353*    (2006.01)
*A61K 9/00*     (2006.01)
*A61P 29/00*    (2006.01)

(52) U.S. Cl.
CPC .......... *A61K 31/353* (2013.01); *A61K 9/0014* (2013.01); *A61P 29/00* (2018.01)

(58) Field of Classification Search
CPC ...... A61K 31/353; A61K 9/0014; A61P 29/00
USPC ....................................................... 514/455
See application file for complete search history.

(56) References Cited

U.S. PATENT DOCUMENTS

| 2007/0197567 A1 | 8/2007 | Sherris |
| 2010/0323985 A1 | 12/2010 | Moutet et al. |
| 2018/0256471 A1 | 9/2018 | Rinsch |

FOREIGN PATENT DOCUMENTS

| EP | 2068864 B1 | 8/2017 |
| JP | 2017007951 A | 1/2017 |
| WO | 2007/133249 A2 | 11/2007 |
| WO | 2014/004902 A2 | 1/2014 |
| WO | 2015/097231 A1 | 7/2015 |
| WO | 2018/162645 A1 | 9/2018 |

OTHER PUBLICATIONS

Smith et al., Fibroblasts as Sentinel Cells Synthesis of Chemokines and Regulation of Inflammation, Amenican Journal of Pathology, vol. 151(2):317-322 (2017).
Barker et al., Keratinocytes as initiators of inflammation, The Lancet, 337:211-214 (1991).
Waasdorp et al., The Bigger Picture: Why Oral Mucosa Heals Better Than Skin, Biomolecules, 11(1165)Jan. 22, 2021.
Callender et al., Postinflammatory Hyperpigmentation Etiologic and Therapeutic Considerations, Am J Clin Dermatol, 12 (2): 87-99 (2011).
Deng et al., The Inflammatory Response in Psoriasis: a Comprehensive Review, Clinic Rev Allerg Immunol, pp. 1-13 (2016).
Hwang et al., Updated understanding of *Staphylococcus aureus* in atopic dermatitis: From virulence factors to commensals and clonal complexes, Experimental Dermatology. 00:1-14 (2021).
Iwamoto et al., *Staphylococcus aureus* in atopic dermatitis: Strain-specific cell wall proteins and skin immunity, Allergology International 68:309-315 (2019).
Kim et al., Interactions Between Atopic Dermatitis and *Staphylococcus aureus* Infection: Clinical Implications, Allergy Asthma Immunol Res., 11(5):593-603 (2019).
Langan et al., Atopic dermatitis, Lancet, 396: 345-60 (2020).
Kim et al., Molecular Mechanism of Atopic Dermatitis Induction Following Sensitization and Challenge with 2,4-Dinitrochlorobenzene in Mouse Skin Tissue, Toxicol. Res., 34(1):7-12 (2018).
Yadav et al., Protein biomarker for psoriasis: A systematic review on their role in the pathomechanism, diagnosis, potential targets and treatment of psoriasis, International Journal of Biological Macromolecules, pp. 1-71 (2018).
Moon et al., In Vitro Models Mimicking Immune Response in the Skin, Yonsei Med J, 62(11):969-980 (2021).
Yang et al., Anti-Inflammatory effects of Perillae Herba ethanolic extract against TNF-α/IFN-γ-stimulated human keratinocyte HaCaT cells, Journal of Ethnopharmacology, pp. 1-28 (2017).

(Continued)

*Primary Examiner* — Kristin A Vajda
(74) *Attorney, Agent, or Firm* — FISHERBROYLES, LLP; Roger L. Browdy

(57) ABSTRACT

The invention relates to the compound urolithin A and its compositions for topical use in inflammatory skin conditions of various etiologies. Anti-inflammatory activity has been demonstrated in vivo in a model of inflammation of the ear caused by infiltration with dinitrochlorobenzene in rats. Topical application of an ointment containing 0.2 and 1.0% urolithin A resulted in a decrease in ear edema and scratching frequency, which was associated with a decrease in the number of immune cells responsible for the progression of inflammation. The results obtained indicate the possibility of using a composition containing urolithin A in local therapy of skin inflammations, in treatment of which hydrocortisone or other steroids are currently used.

19 Claims, 15 Drawing Sheets

(56) References Cited

OTHER PUBLICATIONS

Jung et al., Suppression of thymus- and activation-regulated chemokine (TARC/CCL17) production by 3-O-b-D-glucopyanosylspinasterol via blocking NF-jB and STAT1 signaling pathways in TNF-a and IFN-c-induced HaCaT keratinocytes, Biochemical and Biophysical Research Communications 427:236-241 (2012).
Black et al., Human keratinocyte induction of rapid effector function in antigen-specific memory CD4+ and CD8+ T cells, Eur. J. Immunol., 37:1485-1493 (2007).
De Vos et al., Post-Transcriptional Regulation of Interleukin-6 Gene Expression in Human Keratinocytes by Ultraviolet B Radiation, The Society for Investigative Dermatology, Inc., 103(1):92-96 (1994).
Kim et al., Protective effect of ixerisoside A against UVB-induced pro-inflammatory cytokine production in human keratinocytes, International Journal of Molecular Medicine 35:1411-1418 (2015).
D'Amico, F., Granata, M., Skarmoutsou, E., Trovato, C., Lovero, G., Gangemi, P., Longo, V., Pettinato, M., Mazzarino, M.C., "Biological therapy downregulates the heterodimer 5 S100A8/A9 (calprotectin) expression in psoriatic patients", . Inflamm Res 67, pp. 609-616. (2018).
Furue, K., Ito, T., Tsuji, G., Kadono, T., Nakahara, T., Furne, M, "Autoimmunity and autoimmune co-morbidities in psoriasis", Immunology 154, pp. 21-27. (2018).
Liu, C.F., Li, X.L., Zhang, Z.L., Qiu, L., Ding, S.X., Xue, J.X., Zhao, G.P., Li, J., "Antiaging Effects of Urolithin a on Replicative Senescent Human Skin Fibroblasts", Rejuvenation Res 22, pp. 191-200 (2018).
Papier, A., Strowd, L.C., "Atopic dermatitis: a review of topical nonsteroid therapy", Drugs Context 7, 212521, 2018.
Tomas-Barberan, F.A., Selma, M.V., Espin, J.C., "Polyphenols' Gut Microbiota Metabolites: Bioactives or Biomarkers?", Journal of Agricultural and Food Chemistry 66, pp. 3593-15 94 (2018).
Yadav, K., Singh, D., Singh, M.R., "Protein biomarker for psoriasis: A systematic review on their role in the pathomechanism, diagnosis, potential targets and treatment of psoriasis", Int J Biol Macromol 118, pp. 1796-1810 (2018).
Pastore, S., Mascia, F., Mariotti, F., Dattilo, C., Mariani, V., Girolomoni, G., "ERKI/2 Regulates Epidermal Chemokine Expression and Skin Inflammation", J Immunol 17 4, pp. 504 7-505 (2005).
Tomas-Barberan, F.A., Gonzalez-Sarrias, A., Garcia-Villalba, R., Nunez-Sanchez, M.A., Selma, M.V., Garcia-Conesa, M.T., Espin, J.C., "Urolithins, the rescue of "old" metabolites to understand a "new" concept: Metabotypes as a nexus among phenolic metabolism, microbiota dysbiosis, and host health status", Mol Nutr Food Res 61, 1500901 (2017).
Deng, Y., Chang, C., Lu, Q., "The Inflammatory Response in Psoriasis: a Comprehensive Review", Clin Rev Allergy Immunol 50, pp. 377-389. (2016).
Eichenfield, L.F.M., Friedlander, S.F.M., Simpson, E.L.M.M., Irvine, A.D.M., "Assessing the New and Emerging Treatments for Atopic Dermatitis" Semin Cutan Med Surg 35, pages S92-96 (2016).
Piwowarski, J.P., Granica, S., Stefanska, J., Kiss, A.K., "Differences in Metabolism of Ellagitannins by Human Gut Microbiota ex Vivo Cultures", J Nat Prod 79, pp. 3022-3030. (2016).
Pruenster, M., Vogl, T., Roth, J., Sperandio, M., "SIO0A8/A9: From basic science to clinical application", Pharmacol Ther 167, pp. 120-131 (2016).
Weidinger, S., Novak, N., "Atopic dermatitis" Lancet 387, pp. 1109-1122 (2016).
Piwowarski, J.P., Kiss, A.K., "Contribution of C-glucosidic ellagitannins to Lythrum salicaria L. influence on pro-inflammatory functions of human neutrophils", J Nat Med 69, pp. 100-110 (2015).
Piwowarski, J.P., Kiss, A.K., Granica, S., Moeslinger, T. "Urolithins, gut microbiotaderived metabolites of ellagitannins, inhibit LPS-induced inflammation in RAW 264.7 murine macrophages", Mol Nutr Food Res 59, pp. 2168-2177 (2015).
Tuohy, K., Del Rio, D., "Diet-Microbe Interactions in the Gut. Effects on Human Health and Disease", Elsevier (2015).
Jin, S., Park, C.O., Shin, J.U., Noh, J.Y., Lee, Y.S., Lee, N.R., Kim, H.R., Noh, S., Lee, Y., Lee, J.H., Lee, K.H., "Damp molecules SIO0A9 and SIO0A8 activated by IL-17A and 5 house-dust mites are increased in atopic dermatitis" Exp Dermatol 23, pp. 938-941 (2014).
Piwowarski, J.P., Granica, S., Kiss, A.K., "Influence of gut microbiota-derived ellagitannins' metabolites urolithins on pro-inflammatory activities of human neutrophils", Planta Med 80, pp. 887-895 (2014).
Piwowarski, J.P., Granica, S., Zwierzynska, M., Stefanska, J., Schopohl, P., Melzig, M.F., Kiss, 10 A.K., "Role of human gut microbiota metabolism in the anti-inflammatory effect of traditionally used ellagitannin-rich plant materials", J Ethnopharmacol 155, pp. 801-809 (2014).
'Colombo, E., Sangiovanni, E., Dell'agli, M., "A review on the anti-inflammatory activity of pomegranate in the gastrointestinal tract. Evidence-based complementary and alternative medicine: eCAM 2013", 247145 (2013).
D'Orazio, J., Jarrett, S., Amaro-Ortiz, A., Scott, T., "UV radiation and the skin" Int J Mol Sci 14, pp. 12222-12248 (2013).
Espin, J.C., Larrosa, M., Garcia-Conesa, M.T., Tomas-Barberan, F., "Biological significance of urolithins, the gut microbial ellagic Acid-derived metabolites: the evidence so far. Evidence-based complementary and alternative medicine: eCAM 2013", 270418 (2013).
Haiser, H.J., Turnbaugh, P. J., "Developing ametagenomic view ofxenobiotic metabolism", Pharmacological research 69, pp. 21-31 (2013).
Schonthaler, H.B., Guinea-Viniegra, J., Wculek, S.K., Ruppen, I., Ximenez-Embun, P., GuioCarrion, A., Navarro, R., Hogg, N., Ashman, K., Wagner, E.F., "SIO0A8-SIO0A9 protein complex mediates psoriasis by regulating the expression of complement factor C3", Immunity 39, pp. 1171-1181 (2013).
Bengtsson, A.A., Sturtelt, G., Lood, C., Ronnblom, L., van Vollenhoven, R.F., Axelsson, B., Sparre, B., Tuvesson, H., Ohman, M.W., Leanderson, T., Pharmacokinetics, tolerability, and preliminary efficacy of paquinimod (ABR-215757), a new quinoline-3-carboxamide derivative: studies in lupus-prone mice and a multicenter, randomized, double-blind, placebo-controlled, repeat-dose, dose-ranging study in patients with systemic lupus erythematosus:, Athritis Rhem. May 2012; 64(5) : 1579-88.
Comi, G., Jeffery, D., Kappas, L., Montalban, X., Boyko, A., Rocca, M.A., Filippi, M., Group, A.S., "Placebo-controlled trial of oral laquinimod for multiple sclerosis", N Engl J Med 366, pp. 1000-1009 (2012).
Ishimoto, H., Shibata, M., Myojin, Y., Ito, H., Sugimoto, Y., Tai, A., Hatano, T., "In vivo anti-inflammatory and antioxidant properties of ellagitannin metabolite urolithin A", Bioorg Med Chem Lett 21, pp. 5901-5904 (2011).
Larrosa, M., Garcia-Conesa, M.T., Espin, J.C., Tomas-Barberan, F.A., "Ellagitannins, ellagic acid and vascular health" Molecular aspects of medicine 31, pp. 513-539 (2010).
Larrosa, M., Gonzalez-Sarrias, A., Yanez-Gascon, M.J., Selma, M.V., Azorin-Ortuno, M., Toti, S., Tomas-Barberan, F., Dolara, P., Espin, J.C., "Anti-inflammatory properties of a pomegranate extract and its metabolite urolithin-A in a colitis rat model and the effect of colon inflammation on phenolic metabolism", J N utr Biochem 21, pp. 717-725 (2010).
Bialonska, D., Kasimsetty, S.G., Khan, S.I., Ferreira, D., "Urolithins, intestinal microbial metabolites of Pomegranate ellagitannins, exhibit potent antioxidant activity in a cell-based assay", J Agric Food Chem 57, pp. 10181-10186 (2009).
Bjork, P., Bjork, A., Vogl, T., Stenstrom, M., Liberg, D., Olsson, A., Roth, J., Ivars, F., 5 Leanderson, T., "Identification of human SIO0A9 as a novel target for treatment of autoimmune disease via binding to quinoline-3-carboxamides", PLoS Biol 7, e97 (2009).
Odhiambo, J.A., Williams, H.C., Clayton, T.O., Robertson, C.F., Asher, M.I., Group, I.P.T.S., 'Global variations in prevalence of eczema symptoms in children from ISAAC Phase Three:, J Allergy Clin Immunol 124, pp. 1251-1258 e1223 (2009).
Breneman, D., Fleischer, A.B., Jr., Abramovits, W., Zeichner, J., Gold, M.H., Kirsner, R.S., Shull, T.F., Crowe, A.W., Jaracz, E., Hanifin, J.M., Tacrolimus Ointment Study, G., "Intermittent therapy for flare prevention and long-term disease control in stabilized atopic dermatitis: a randomized comparison of 3-times-weekly

(56) References Cited

OTHER PUBLICATIONS applications of tacrolimus ointment versus vehicle", J Am Acad Dermatol 58, pp. 990-999 (2008).

Berth-Jones, J., Damstra, R.J., Golsch, S., Livden, J.K., Van Hooteghem, 0., Allegra, F., Parker, C.A., Multinational Study, G., "Twice weekly fluticasone propionate added to emollient maintenance treatment to reduce risk of relapse in atopic dermatitis: randomised, double blind, parallel group study", BMJ 326, 1367 (2003).

D'Haens, G., Sandborn, W.J., Colombel, J.F., Rutgeerts, P., Brown, K., Barkay, H., Sakov, A., Raviv, A., Feagan, B.G., Laquinimod for Crohn's Disease, I., "A phase II study of laquinimod in Crohn's disease", Gut 64, pp. 1227-1235 (2014).

UROLITHIN A AND A COMPOSITION CONTAINING SAME FOR EXTERNAL USE IN INFLAMMATIONS OF VARIOUS ETIOLOGIES

FIELD OF THE INVENTION

The invention relates to the compound, urolithin A, administered topically in inflammations of various etiologies and to the composition containing urolithin A acting by reduction of the level of S100A8/A9 (calprotectin) and stimulating phosphorylation of MAP ERK1/2 kinases.

BACKGROUND OF THE INVENTION

Skin inflammations of various etiologies affect a large part of society. Atopic dermatitis (AD) occurs in about 20% of children and 7% of adults. A particular increase in the incidence of atopic dermatitis is observed in developed countries (Odhiambo et al., 2009). The pathogenesis of AD is very complex. It involves cells of the specific inflammatory response system (T cells, mast cells) as well as cells of the non-specific inflammatory response system (neutrophils, macrophages). It is currently believed that Th2 lymphocytes producing IL-4, IL-5, and IL-13, which secretion is associated with increased production of immunoglobulin E, play a major role in the course of AD (Eichenfield et al., 2016).

Psoriasis is a disease affecting 2-5% of the world population. It is associated with hyperproliferation and hyperkeratosis of epidermal cells. As a consequence, epidermal thickening and inflammatory infiltration of neutrophils, macrophages, dendritic cells and T cells in the dermis occur. The main signaling pathways responsible for the development of psoriatic lesions in the skin are: the S100 protein pathway (including S100A8/A9), the Wnt pathway, the JAK-STAT pathway, and the RAR pathway (Yadav et al., 2018).

Etiology of skin inflammations is very complex and dependent on the interaction between skin cells—keratinocytes and fibroblasts—and immune cells—mast cells, lymphocytes, monocytes, macrophages, neutrophils, and dendritic cells. In recent years, the dimeric protein—calprotectin—has begun to be attributed a special role in skin inflammations of various etiologies including atopic dermatitis and psoriasis (D'Amico et al., 2018; Jin et al., 2014; Schonthaler et al., 2013). Heterodimeric protein S100A8/A9 (calprotectin, calgranulin) is currently considered one of the key factors regulating the inflammatory response. It belongs to the family of $Ca^{2+}$ binding proteins and is found in large quantities in neutrophil cytoplasm (up to 40% of soluble cytosolic proteins) and monocyte cytoplasm (up to 5%). Being passively or actively secreted by neutrophils and macrophages, it performs its effector functions by binding to glycosaminoglycans and to pattern recognition receptors: Toll like receptor 4 (TLR4) and Receptor of Advanced Glycation Endproducts (RAGE) on the surface of endothelial cells, phagocytes and lymphocytes. It has been shown that S100A8/A9 increases secretion of IL-8, IL-6, MCP-1 and adhesion molecules by endothelial cells and contributes to increased monolayer permeability by disorganization of F-actin and inhibiting expression of E-cadherin, zonula occludens-1 (ZO-1) and β-catenin. By interacting with the TLR4 receptor on the surface of neutrophils S100A8/A9 causes a decrease in surface expression of L-selectin (CD62L) and an increase in the level of β2 integrin (CD11b/CD18) which conditions tight adhesion and diapedesis. It has been shown that these effects can be associated with activation of MAPK/ERK kinases and the NF-κB pathway. In addition, S100A8/A9 has also been shown to significantly increase IL-17 production by CD8+ T cells. It is believed that the S100A8/A9 protein alone does not have chemotactic properties, but induces chemotaxis by activating immune cells. The level of S100A8/A9 closely correlates with the progression of inflammation and is therefore often considered an important biomarker in various inflammatory and autoimmune diseases (rheumatism, inflammatory bowel disease, skin inflammation, vasculitis, systemic lupus erythematosus, dermatomyositis, scleroderma, multiple sclerosis, giant cell arteritis, psoriasis, cystic fibrosis, rejection of renal allograft, infections, cardiovascular diseases). Currently, S100A8/A9 is considered to be a key factor stimulating inflammatory response, regulation of which may suppress functions of immune cells responsible for progression of inflammatory and autoimmune diseases (Pruenster et al., 2016).

Recently published research results indicate that S100A8/A9 may be an interesting target in development of new therapies for inflammatory diseases. To date, only compounds from the group of quinoline-3-carboxamide derivatives have been shown to inhibit the interaction of S100A8/A9 with the TLR4 receptor (Bjork et al., 2009). It is also important that in clinical studies said compounds showed activity against multiple sclerosis (Comi et al., 2012), lupus erythematosus (Bengtsson et al., 2012) and Crohn's disease (D'Haens et al., 2015).

It has been shown that in skin inflammations, decrease of ERK1/2 kinase activity is of great importance, as it leads to stabilization of mRNA for proinflammatory cytokines and in consequence to an increase in production of thereof and progression of inflammation. Therefore, stimulation of the ERK1/2 phosphorylation pathway may be an important goal when developing new therapeutic strategies for skin inflammations of various etiologies (Pastore et al. 2005).

In recent years, knowledge about the role of intestinal microbiota in maintaining homeostasis in the human body has started to develop dynamically. Activity of intestinal microbiota is considered to be of key importance for health mainly through the effect of nutrients and xenobiotics on the immune system and metabolism (Tuohy and Del Rio, 2015). The research results, which refer to changes in the structure of orally ingested compounds that is influenced by intestinal microbiota, make now necessary, when assessing the impact of substances found in food and drugs on the human body, to take into account biological activity of metabolites formed in the gut (Haiser and Turnbaugh, 2013).

One of the groups of compounds subject to significant structural changes under the influence of intestinal microbiota are ellagitannins, which are high-molecular polyphenols, which are found in food products such as walnuts, hazelnuts, almonds, pomegranate juice, raspberries, strawberries, and oak-aged wine and in many medicinal plant materials. Bioavailability of these compounds in the unchanged state, due to the high-molecular structure and hydrophilic nature and susceptibility to hydrolysis, is not fully established or even is considered doubtful. However, it is known that ellagitannins are metabolized under the influence of intestinal microbiota to dibenzo[b,d]pyran-6-one derivatives, namely urolithins, which unlike ellagitannins, are small-molecular, lipophilic compounds with well-documented bioavailability, which can reach micromolar concentrations in blood, tissues, feces and urine (Espin et al., 2013). Beneficial effects of orally administered elagotannin-rich foods on chronic inflammatory diseases were found in in vivo studies. Positive effects of elagotannin-rich foods on the cardiovascular system and inflammatory bowel disease are particularly highlighted. Due to the metabolism of ellagitannins by the intestinal microbiota, what has been shown in recent years, it is believed that urolithins formed in the intestine may be responsible for the observed effects (Colombo et al., 2013; Larrosa et al., 2010a; Piwowarski et al., 2014b; Tomas-Barberan et al., 2016).

Skin inflammations of various etiologies affect a large part of society. Atopic dermatitis occurs in 20% of children and 7% of adults and is common in both developed and developing countries. Topical steroids, including hydrocortisone, are the first-line medications for AD and psoriasis. Indications for topical use of hydrocortisone and other steroid drugs are skin diseases such as lupus erythematosus, erythema multiforme, seborrheic dermatitis; insect bites (for reducing pain, itching and swelling discomforts after bites, especially if subject is allergic to biting insect venom); acne (eczemas); skin changes caused by taking medications; first- and second-degree burns; itchy skin; skin blushing. However, the use of steroid drugs is associated with serious side effects such as bacterial and fungal infections, skin atrophy, changes in skin pigmentation, telangiectasia, and the risk of acting on the hypothalamic-pituitary-adrenal axis (especially in children). In addition, the effectiveness of steroid drugs is limited by the occurrence of tachyphylaxis (weakening of the effect which is caused by prolonged use of the drug), which limits the effectiveness in the treatment of chronic skin inflammations. When steroid therapy is ineffective or cannot be used due to existing hypersensitivity, calcineurin inhibitor therapy (tacrolimus, pimecrolimus) is introduced. It can only be carried out for a short time and is associated with an increased risk of cancer (non-melanoma skin cancer and lymphoma) and is associated with an increased risk of viral infections, e.g. Herpes simplex. In the case of topical AD treatment with both steroid drugs and calcineurin inhibitors, the disease in most cases relapses after six months at the latest (Berth-Jones et al., 2003; Breneman et al., 2008; Papier and Strowd, 2018).

The present invention provides urolithin A and a composition containing same for local inhibition of inflammation.

Urolithin A belongs to dibenzo[b,d]pyran-6-one derivatives. It is a metabolite produced by intestinal microbiota from tannins belonging to the ellagitannins group found in some food products, i.e. pomegranate fruits, strawberries, raspberries, walnuts or in wine ripening in oak barrels. Unlike ellagitannins from which it is formed, urolithin A is a small molecule, lipophilic compound of a well-documented bioavailability. Upon absorption in the intestine, urolithin A is conjugated to glucuronic acid and hence is present in the form of glucuronides in both tissues and the bloodstream. It is known that not all people produce each and every type of urolithin. Studies published so far show that there are people producing as the dominant compound either urolithin A, iso-urolithin A or urolithin B or not producing urolithins at all (Piwowarski et al., 2016; Tomas-Barberan et al., 2017). Urolithin A is distinguished from iso-urolithin A by the orientation of hydroxyl groups, while their number distinguishes urolithin B from urolithin C. With such a small molecule, a slight change in the arrangement and amount of hydroxyl groups is crucial for the activity of the compound. Studies carried out so far indicate that both the number and orientation of hydroxyl groups determine changes in the biological activity of individual compounds (Piwowarski et al., 2014a; Piwowarski et al., 2015).

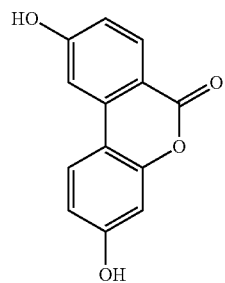

iso-urolithin A

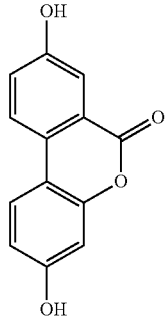

urolithin A

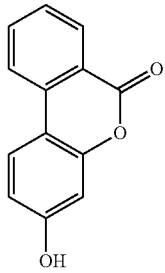

urolithin B

Urolithin A is a metabolite formed in the large intestine from compounds found in food under the influence of intestinal microbiota. Its concentration in feces, tissues, blood and urine following ingestion food products rich in ellagitannins can reach 100 µM. Based thereon, it can be concluded that the external use of this compound involves very little risk of toxic effects or severe side effects, including also chronic exposure of the body to this substance. The problem that arises with the use of endogenous urolithin A is the fact that not every human has bacteria capable of producing urolithin A. In addition, the organisms responsible for this process have yet to be identified, which prevents manipulation of the composition of intestinal microbiota to induce the production of urolithin A in the large intestine. On the other hand, direct oral administration of urolithin A does not allow therapeutic concentrations to be achieved by this compound, because during transport through the gastrointestinal tract it undergoes further dehydroxylation leading to the formation of urolithin B. In turn, urolithin A, either administered orally or endogenously produced, undergoes intensive metabolism while passing through the intestinal wall. Phase II metabolism consists in coupling of some xenobiotics with reactive metabolites in the body, making them more soluble in the aqueous environment of body fluids and, as a consequence, more easily excreted in the urine. Coupling reactions occurring in the phase II of biotransformation are catalyzed mainly by enzymes from the class of transferases, and metabolites that participate in these reactions are amino acids, glutathione, and activated acids, i.e. acetic, sulfuric and, especially, glucuronic acid. As a consequence of this process, it is not free urolithin A, but its forms conjugated with glucuronic acid, that are present in the bloodstream and tissues. As shown in previous in vitro studies, both dehydroxylation and glucuronidation of urolithin A may lead to a change or loss of activity (Tomas-Barberan et al., 2017; Tomas-Barberan et al., 2018).

Above restrictions associated with the metabolism of ellagitannins and urolithin A related to their oral use have led to attempts to use anti-inflammatory properties of urolithin A in a topical composition applied to the skin. Application of the compound directly to the skin circumvents the problem of deactivation under the influence of phase II enzymes and results in achieving active concentrations of the compound directly at the site of inflammation, which are not possible to achieve with normal consumption of foods containing ellagitannins or with oral administration of urolithin A.

Further, the studies published in July 2017 indicate no toxicity of urolithin A in an animal model upon both oral and intravenous administration (Heilman et al. 2017 Food and Chemical Toxicology doi: 10.1016/j.fct.2017.07.050). Moreover, urolithin A is a compound with a completely different mechanism of action as compared to the steroid drugs and calcineurin inhibitors used in therapy so far, i.e. it inhibits the release of calprotectin and inhibits the translocation of the NF-κB subunit into the nucleus (Piwowarski et al., 2015).

An advantageous aspect is also the fact that urolithin A is an effective alternative to currently used steroid drugs and calcineurin inhibitors, which show low efficiency in many cases of inflammatory and autoimmune diseases of skin/mucous membranes. The use of steroid drugs is associated with the occurrence of tachyphylaxis effect, i.e. a decrease in the effectiveness of the drug caused by its frequent use, which limits its effectiveness in treatment of chronic inflammations. This effect is characteristic of drugs which action is based on the receptor-mediated mechanism. Urolithin A is a substance that inhibits secretion of calprotectin and inhibits the signaling pathway associated with the translocation process of the p65 subunit of NF-κB to the nucleus and has not been shown as yet to have receptor activity, and therefore the tachyphylaxis effect for urolithin A should not limit its effectiveness in chronic use.

In view of the fact that urolithin A is a compound produced in the intestine from ellagitannins found in typical food products, there is a low risk of toxic effects or serious adverse effects in vivo also with chronic exposure to this substance.

It should also be emphasized that reduced risk of side effects from external use of urolithin A will affect significantly the results of therapy, which will not generate additional costs associated with further treatment. In 16-43% of patients using topical steroids, bacterial and fungal infections are observed within the areas being treated, which infections must be treated pharmacologically. Skin atrophy, changes in pigmentation (hypo- and hyperpigmentation) and contact hypersensitivity to steroids have been also described, which make further therapy impossible. Therapy with calcineurin inhibitors may only be carried out for a short time and is associated with an increased risk of skin cancers.

That is why it is so important the attempt to identify a compound and to prepare a composition containing the compound that would be effective in treatment of cases resistant to conventional therapy and its use would not be associated with the risk of serious adverse effects.

Oral or parenteral use of urolithin A and its systemic therapeutic effects are known in the art.

Publication *Anti-inflammatory properties of a pomegranate extract and its metabolite urolithin-A in a colitis rat model and the effect of colon inflammation on phenolic metabolism* (Larrosa et al., 2010b) concerns the effect of orally administered pomegranate extract at a dose of 250 mg/kg or urolithin A at a dose of 15 mg/kg on intestinal inflammation caused by dextran sulfate sodium in rats. Extract and urolithin A were administered for 25 days, and intestinal inflammation was induced by DSS administration for the last 5 days of the experiment. Based on the results obtained, the authors concluded that in the case of inflamed colon, therapeutic activity is shown mainly by pomegranate extract and its ellagitannins, while the anti-inflammatory activity of urolithin A can only be relevant in healthy individuals. The authors of the study were led to such conclusions by investigation of faecal specimens from animals receiving urolithin A, in which small amounts of this compound were found. It probably underwent further metabolism under the influence of intestinal microbiota or was absorbed and underwent phase II metabolism.

Publication *In vivo anti-inflammatory and antioxidant properties of ellagitannin metabolite urolithin A* (Ishimoto et al., 2011) pertains to the effect of oral administration of urolithin A on carrageenan-induced paw edema in mice. Oral administration of urolithin A one hour after induction of edema significantly reduced its size over the next 24 hours of the experiment. According to the authors, the model used allows to assess the anti-inflammatory potential only for orally administered drugs. At the same time, in plasma the presence of phase II metabolites of urolithin A—glucuronides—were found. So we can conclude that the oral administrated urolithin A is metabolised and hence its metabolism product—urolithin A glucuronide—is responsible for the observed changes.

Patent document EP2068864B1 discloses therapeutic use of urolithin selected from the group consisting of: urolithin B, urolithin A, hydroxy-urolithin A, methyl-urolithin A, for the treatment and/or prevention of cancer in a subject. It is known that metabolites of ellagitannins have antiproliferative and/or proapoptotic activity and as such find use in the treatment and prevention of many cancers. However, in contrast to the above, the invention being the subject of the present application discloses the use of urolithin A for skin inflammations. Skin inflammations of various etiologies are related with an increased inflammatory response of immune cells, but they are not cancerous. Inhibition of skin inflammation in vivo by topical administration of a urolithin A composition, as demonstrated by us, is associated with local inhibition of inflammatory processes and is not in connection with an inhibitory effect on cell proliferation or induction of apoptosis therein. Moreover, in previous studies performed on neutrophils and macrophages there was not observed either cytotoxic or antiproliferative activity of urolithin A. (Piwowarski et al., 2014a; Piwowarski et al., 2014b; Piwowarski et al., 2015).

US application US2010323985A discloses the use of a compound from the group of urolithins, urolithin B, as a component of a pharmaceutical or cosmetic preparation for topical and/or parenteral use. However, the document in question does not refer to the use of urolithin B as such, but rather to the combination of hyaluronic acid and at least one hyaluronic acid degradation inhibitor, in particular for dermatological use in humans, and in particular in treatment by filling wrinkles, fine lines, fibroblast defects and any scars or in reconstructive surgery. Urolithin B has been indicated as an example of one of hyaluronic acid degradation inhibitors, alone or in a mixture. With respect to the above, the inventors conducted experiments according to the pharmacopoeial method (USP), observing as a result no effect of urolithin A on hyaluronidase activity. However, inhibitory activity towards said enzyme was observed for ellagitannins, among which urolithin A is produced by intestinal microbiota (Piwowarski and Kiss, 2015). Furthermore, the use of a compound belonging to the urolithin family disclosed in the above application does not refer to atopic dermatitis, as there is no literature data confirming increased degradation of hyaluronic acid in this condition. Also, in the case of psoriasis, research is currently underway on effectiveness of hyaluronidase subcutaneous injections (Hylenex preparation; https://clinicaltrials.gov/ct2/show/NCT01987609).

Japanese Patent Application JP2017007951A relates to a new use of urolithins in inhibiting photoaging caused by the influence of UV radiation on the skin. The description of the application discloses a general formula for urolithins, indicating a joint effect for urolithins, e.g., urolithin A, urolithin B, urolithin C, urolithin D, urolithin E, urolithin M3, urolithin M4 and the like, in inhibiting photoaging. The properties of urolithin A described by the inventors in the application relate to the direct protection of the skin against UV radiation, which is associated only with the physicochemical and not pharmacological properties of the molecule. Exposure to UV radiation as a tissue damaging factor accelerates skin aging and excessive one-time exposure to radiation can cause skin inflammation (sunburn) and cancers (D'Orazio et al., 2013). Urolithin A is used herein as a compound absorbing UV radiation and thus preventing skin damaging action, which indirect consequence upon acute exposure is inflammation of the skin caused by e.g. sunburn. The application relates in particular to the prevention of dermatitis caused by excessive exposure to UV radiation, and does not relate to other inflammatory conditions. There are no known literature reports of induction atopic dermatitis or psoriasis by UV radiation. Moreover, there is known widespread use of UV radiation in phototherapy for atopic dermatitis and psoriasis.

International patent application (WO2014004902 A2) relates to the use of compounds from the group of urolithins and their precursors as substances that stimulate autophagy and thus inhibit aging processes. The application is based on the results of in vitro and in vivo tests that indicate urolithins as compounds that promote autophagy and thus prevent aging processes, increase the strength of animal muscles and their locomotor activity. In vivo studies were conducted only for orally administered urolithin A and did not include test of urolithin A metabolism in the gastrointestinal tract of animals and under the influence of phase II enzymes. Due to recognized autophagy stimulating effect following oral administration, the present inventors presume that compounds belonging to the urolithin group may be used in the treatment of conditions in which stimulation of this process is desirable. Among many conditions, skin diseases are also mentioned: skin aging, photoaging, skin inflammation and psoriasis, as those in which stimulation of the autophagy process may prove beneficial. However, no studies have been conducted that would indicate anti-inflammatory activity of urolithin A following topical application to the skin, and no processes that are key to the development of skin inflammations of various etiologies, including atopic dermatitis and psoriasis, were included in the studies.

In contrast to the above described international application, the essence of the present invention is direct anti-inflammatory action on the skin, as described in the in vivo model, associated with accelerating the healing process, reducing scratching frequency and reducing the population of immune cells responsible for the progression of inflammation (leukocytes, monocytes and neutrophils) which may be connected with inhibition of calprotectin release. The above processes are not related to the previously described autophagy stimulating effect of urolithin A following oral administration. In addition, according to the available literature, inhibition of the autophagy process is not crucial for the progression of skin inflammations of various etiologies including psoriasis, neither the role of the autophagy process in the etiology of atopic dermatitis is known (Deng et al., 2016; Furue et al., 2018; Weidinger and Novak, 2016; Yadav et al., 2018).

The results obtained and described in the above patent application are also referred to in international patent application (WO2015097231A1), disclosing the use of compounds from the group of amino acid derivatives of urolithins as substances having higher solubility than urolithins and releasing urolithins in the gastrointestinal tract following oral administration. The results presented in the application were connected with properties that promote autophagy and thus inhibit the aging processes what is described for oral urolithins. However, unlike the above, the present application relates to direct anti-inflammatory effects on the skin associated with accelerating the healing process, reducing scratching frequency and reducing the response from immune cells responsible for progression of inflammation. These processes are completely unrelated to previously described stimulating effects of urolithin A on autophagy following oral administration. In addition, according to the available literature, inhibition of the autophagy process is not crucial for the progression of skin inflammations of various etiologies including psoriasis, and the role of the autophagy process in the etiology of atopic dermatitis is also unknown (Deng et al., 2016; Furue et al., 2018; Weidinger and Novak, 2016; Yadav et al., 2018).

In turn, international patent application WO2018162645 relates to the topical use of preparations containing urolithins in reducing skin hyperpigmentation. The studies were conducted in in vitro conditions, in which urolithin A caused reduced production of melanin in skin cells.

Similarly, in scientific paper *Antimelanogenic Effect of Urolithin A and Urolithin B, the Colonic Metabolites of Ellagic Acid, in B16 Melanoma Cells* (Shang-Ta Wang et al., 2017) it has been described that urolithin A (UA) and B (UB), the main metabolites of dietary ellagic acid derivatives produced by the intestinal microbiota, show efficiency in depigmentation by suppressing tyrosinase activity.

However, skin hyperpigmentation is dependent not only on the etiology of inflammatory skin and mucosal diseases, and its inhibition is not the purpose of the present invention, but it differs depending on the background of the disease. Unlike for hyperpigmentation which results from disorders of synthesis and distribution of natural melanin pigment in the skin, the immediate cause of atopic dermatitis and psoriasis is an increased response from the immune system. The present application discloses anti-inflammatory effect of urolithin A on the skin that can be used to treat atopic dermatitis and psoriasis that do not result from skin hyperpigmentation (Deng et al., 2016; Furue et al., 2018; Weidinger and Novak, 2016; Yadav et al., 2018).

Therefore, in the light of the above, a person skilled in the art would not be motivated and could not, without creative input, reach the solution of the present invention, i.e. the use of urolithin A in inflammatory conditions of the skin.

Furthermore, US application US20070197567A1 and international application WO2007133249A2 relate to the use of benzo[c]chromen-6-one derivatives in treatment of skin diseases associated with excessive cell proliferation and angiogenesis. Excessive proliferation of fibroblasts and keratinocytes, and increased angiogenesis, described by the authors of the above applications are secondary to skin inflammation, but they are not the underlying cause. The immediate cause of atopic dermatitis and psoriasis is increased immune response, hence the present application discloses anti-inflammatory effect of urolithin A on the skin that can be used to treat atopic dermatitis and psoriasis. In addition, comparative studies carried out by the present inventors confirmed that neither urolithin A, nor 8-acetyl-urolithin A, nor 3-acetyl-urolithin A showed antiproliferative activity on human skin fibroblast cells in contrast to the tested acetylated urolithin B derivative.

Publication *Anti-aging Effects Of Urolithin A On Replicative Senescent Human Skin Fibroblasts* (Liu et al., 2018) relates to the studies of urolithin A effect on aging processes carried out in an in vitro model of human fibroblasts. The authors showed that urolithin A stimulated collagen synthesis and inhibited the mRNA expression for matrix metalloproteinase-1, and additionally they have demonstrated antioxidative activity dependent on activation of the Nrf2 receptor. Whereas, no inhibition of fibroblast aging was found. Nevertheless, based on in vitro studies, the authors suggest cosmetic use of urolithin A in anti-aging preparations. The above studies were carried out on cells that are part of skin tissue, but the study design does not relate to phenomena and mechanisms related directly to skin inflammations.

In addition, topical use of urolithin A on the skin has not yet been described for application in the treatment of skin inflammation. The patent applications and publications cited above are based solely on in vitro and in vivo studies following oral administration of urolithin A. The route of administration of urolithin A is of particular importance considering metabolism of urolithin A occurring in the gastrointestinal tract following oral administration. To date, no in vivo studies have been performed on the topical use of urolithin A or any of the other compounds belonging to the urolithin group. These reports are also confirmed by the publication on Mar. 20, 2018 a critical commentary by pioneers of research on urolithins (Tomas-Barberan et al., 2018) and those skilled in the art of intestinal microbiota metabolism, and a review article published by them a year earlier (Tomas-Barberan et al., 2017) clearly indicating that direction of anti-inflammatory effects on the skin and topical application of urolithin A has not been taken into account yet. Therefore, the results obtained along with the present application are the first report on the use of urolithin A, which is a metabolite of intestinal microbiota, and a composition containing same for local inhibition of inflammation.

SUMMARY OF THE INVENTION

With the above in mind, the goal for the present inventors was to provide such an active substance that will be easy to process, cheap to manufacture, and thus easily available, and which effectively reduces the level of S100A8/A9, i.e. calprotectin, and stimulates phosphorylation of ERK1/2 kinases, which will be suitable for external application to the skin and mucous membranes, demonstrating desired anti-inflammatory effect, relieving the symptoms of inflammations and preventing them from occurring. Furthermore, the object of the invention was that the active substance provided is suitable for delivery as a useful composition for self-use by a subject in need thereof, and is persistent, does not degrade, and is stable over time. The present inventors have surprisingly found that this object can be achieved by using as an active ingredient such urolithin A composition, or a pharmaceutically acceptable derivative or prodrug thereof.

Essence of the Invention

The present invention provides a pharmaceutical composition comprising one or more typical auxiliary substances and an active ingredient, which composition comprises urolithin A or a pharmaceutically acceptable derivative thereof as active ingredient, for use in the treatment, inhibition and prevention of inflammatory skin and/or mucosal diseases. Preferably urolithin A is synthetic urolithin A. The preferred urolithin A derivative may be urolithin A 3-formate, urolithin A 8-acetate, urolithin A 3-acetate, urolithin A 3,8-diacetate, urolithin A 8-propionate, urolithin A 8-butyrate, urolithin A 3,8-diisobutyrate, urolithin A 3,8-disalicylate, urolithin A 8-benzoate, urolithin A 8-citrate, urolithin A 8-stearate, urolithin A 3,8-palmitate, urolithin A 8-oleate, urolithin A 3,8-didodecanoate. Preferably urolithin A derivative may be selected from the group of diacylated derivatives. Preferably urolithin A derivative can be selected from the group consisting of urolithin A 8-acetate, urolithin A 3-acetate and urolithin A 3,8-diacetate, most preferably urolithin A derivative is urolithin A 3,8-diacetate. The active ingredient is present in the composition of the invention in an amount of from about 0.0001 weight percent to about 15 weight percent based on the total weight of the composition, preferably from about 0.01 weight percent to about 5 weight percent based on the total weight of the composition, more preferably from about 0.1 weight percent to about 2 percent by weight based on the total weight of the composition, most preferably 1 percent by weight based on the total weight of the composition.

In one preferred embodiment, the pharmaceutical composition of the invention further comprises at least one drug selected from the group of steroids, calcineurin inhibitors, drugs with antibacterial, antifungal or antiviral activity, preferably selected from the group of steroids or calcineurin inhibitors, most preferably the drug is a calcineurin inhibitor.

In another preferred embodiment, urolithin A is the only active ingredient present in the composition.

Preferably, in the pharmaceutical composition of the invention, the at least one pharmaceutically acceptable auxiliary substance is selected from a carrier and/or excipient and/or diluent and combinations thereof. Preferred pharmaceutically acceptable auxiliary substance is one or more of protective agents, adsorbents, demulcents, emollients, preservatives, antioxidants, moisturizers, buffering agents and solubilizing agents.

In preferred embodiment, the pharmaceutical composition of the invention is intended for external administration, more preferably for topical administration, preferably with diseased area being in the range from about 0.0001 $g/cm^2$ of skin surface area to about 0.5 $g/cm^2$, preferably from 0.001 $g/cm^2$ to about 0.2 $g/cm^2$ of skin surface area.

Preferably, the composition of the invention is in a liquid form. Equally preferably, the composition of the invention is in the form of a tonic, balm, lotion, foam, most preferably in the form of a tonic.

Equally preferably, the pharmaceutical composition of the invention is in semi-solid form, preferably in the form of an ointment, cream, paste, gel, preferably in the form of an ointment or cream, most preferably in the form of an ointment.

In an even more preferred embodiment, the composition of the invention is intended to be applied to the diseased area manually, preferably using a dropper, application stick or spray applicator.

In yet a further embodiment, the pharmaceutical composition of the invention is in the form of a transdermal therapeutic system such as an intradermal patch or a transdermal patch.

The subject of the present invention is the pharmaceutical composition according to the invention for use in the treatment, inhibition and prevention of inflammatory diseases of skin and/or mucous membranes, wherein particularly preferred diseases of skin and/or mucous membranes are the following diseases selected from the group consisting of skin inflammations, vasculitides, lupus erythematosus, dermatomyositis, scleroderma, multiple sclerosis, giant cell arteritis, psoriasis, atopic dermatitis, seborrheic dermatitis, contact dermatitis, urticaria, rosacea, dermatitis herpetiformis, lichen planus, hidradenitis suppurativa, pityriasis rosea of Gibert, hydrocystoma, aphthae, diaper dermatitis, adolescent acne, non-allergic contact eczema, panniculitis, cellulitis. Particularly preferably, the pharmaceutical composition of the invention is used when the disease of skin and mucous membranes is psoriasis or atopic dermatitis.

The subject of the present invention is also the use of a pharmaceutical composition according to the invention for the treatment of a disease of skin and mucous membranes, which disease of skin and/or mucous membranes is selected from the group consisting of skin inflammations, vasculitides, lupus erythematosus, dermatomyositis, scleroderma, multiple sclerosis, giant cell arteritis, psoriasis, atopic dermatitis, seborrheic dermatitis, contact dermatitis, urticaria, rosacea, dermatitis herpetiformis, lichen planus, hidradenitis suppurativa, pityriasis rosea of Gibert, hydrocystoma, aphthae, diaper dermatitis, adolescent acne, non-allergic contact eczema, panniculitis, cellulitis, wherein especially preferably the composition is used when the disease of skin and mucous membranes is psoriasis or atopic dermatitis.

DETAILED DESCRIPTION OF THE INVENTION

As indicated above, the subject of the present invention is a pharmaceutical composition for external use containing urolithin A as the active ingredient. Preferably, the subject of the present invention is a composition of the invention for external use containing synthetic urolithin A, which in nature is a metabolite of intestinal microbiota. Urolithin A has anti-inflammatory properties used in the treatment of inflammations of skin and mucous membranes.

More specifically, the invention discloses urolithin A for topical use in the treatment, inhibition and prevention of inflammatory diseases of skin and mucous membranes, in particular: skin inflammations, vasculitides, lupus erythematosus, dermatomyositis, scleroderma, multiple sclerosis, giant cell arteritis, psoriasis, atopic dermatitis, seborrheic dermatitis, contact dermatitis, urticaria, rosacea, dermatitis herpetiformis, lichen planus, hidradenitis suppurativa, pityriasis rosea of Gibert, hydrocystoma, aphthae, diaper dermatitis, adolescent acne, non-allergic contact eczema, panniculitis, cellulitis.

As used herein, the term "inflammation" should be understood in accordance with generally accepted meaning as a set of acute or chronic symptoms that persist over time and are associated with an increased immune response within the skin and mucous membranes, including itching, burning, dryness and roughness of the skin, feeling of constringency, tightness of the skin, any type of irritation or patches of discolored skin that require treatment or should be prevented. Inflammation within mucous membranes has a similar etiology and manifests itself in a similar way and may or may not occur together with inflammation within the skin.

The invention also provides pharmaceutical compositions comprising various forms of urolithin A, together with one or more pharmaceutically acceptable excipients, diluents or carriers.

Such a pharmaceutical composition, without being limited to the information provided herein, may contain the solid form according to the invention which is mixed with at least one pharmaceutically acceptable excipient and/or diluent. However, preferably the composition according to the invention has the final formulation which is a liquid or semi-solid form and is usually administered to subject in need thereof in the form of a foam, tonic, ointment, emulsion or cream.

The term "subject" as used herein includes a single biological organism in which inflammation may occur, including, but not limited to, animals, and in particular higher animals, and in particular vertebrates such as mammals, and in particular humans.

Examples of suitable excipients include, but are not limited to, starch, acacia, calcium silicate, microcrystalline cellulose, polyvinylpyrrolidone, cellulose, water, syrup and methylcellulose. The composition may additionally contain lubricants such as, for example, talc, magnesium stearate and mineral oil; wetting agents; emulsifying and suspending agents; preservatives such as methyl- and propylhydroxybenzoates; flavorings.

The topical composition included in the invention may contain pharmaceutically acceptable auxiliary substances, including, but not limited to, protective agents, adsorbents, demulcents, emollients, preservatives, antioxidants, moisturizers, buffering agents, solubilizing agents, skin penetrating agents and surfactants.

Suitable protective agents and adsorbents include, but are not limited to, dusting powders, zinc stearate, collodion, dimethicone, silicones, zinc carbonate, aloe vera gel and other aloe vera products, vitamin E oil, allantoin, glycerin, petrolatum and zinc oxide.

Suitable demulcents include, but are not limited to, benzoin, hydroxypropyl cellulose, hydroxypropyl methyl cellulose, and polyvinyl alcohol.

Suitable emollients include, but are not limited to, animal and vegetable fats and oils, myristyl alcohol, alum, and aluminum acetate.

Suitable preservatives include, but are not limited to, quaternary ammonium compounds such as benzalkonium chloride, benzethonium chloride, cetrimide, dequalinium chloride and cetylpyridinium chloride; mercury agents such as phenylmercuric nitrate, phenylmercuric acetate and thimerosal; alcoholic agents, for example, chlorobutanol, phenylethyl alcohol and benzyl alcohol; antibacterial esters, for example, parahydroxybenzoic acid esters; and other antimicrobials such as chlorhexidine, chlorocresol, benzoic acid and polymyxin. Chlorine dioxide ($ClO_2$), preferably, stabilized chlorine dioxide, is a preferred preservative for use in the topical composition included in invention.

Suitable antioxidants include, but are not limited to, ascorbic acid and its esters, sodium bisulfite, butylhydroxytoluene, butylhydroxyanisole, tocopherols and chelating agents such as EDTA and citric acid.

Suitable moisturizers include, but are not limited to, glycerin, sorbitol, polyethylene glycols, urea, and propylene glycol.

Suitable buffering agents for use in the invention include, but are not limited to, acetate buffers, citrate buffers, phosphate buffers, lactic acid buffers, and borate buffers.

Suitable solubilizing agents include, but are not limited to, quaternary ammonium chlorides, cyclodextrins, benzyl benzoate, lecithin, and polysorbates.

The topical composition included in the invention may further contain drugs from the group of steroids, calcineurin inhibitors and/or phosphodiesterase 4 inhibitors. The composition may also be a combination of urolithin A and a drug/drugs with antibacterial, antifungal or antiviral activity. Drugs from the steroid group include, but are not limited to, clobetasol propionate, betamethasone, halobetasol, desoximetasone, halometasone, acetonide, hydrocortisone, mometasone. Drugs from the calcineurin inhibitors group include, but are not limited to, tacrolimus, pimecrolimus. Drugs from the group of phosphodiesterase 4 inhibitors include, but are not limited to, crisaborole. Antibacterial agents include, but are not limited to, sulfacetamide, bacitracin, neomycin, polymyxin b, erythromycin, mupirocin, gentamicin, chloramphenicol. Antifungal drugs include, but are not limited to, clotrimazole, econazole, miconazole, terbinafine, fluconazole, ketoconazole and amphotericine. Antiviral drugs include, but are not limited to acyclovir, penciclovir, valaciclovir, famciclovir.

The topical composition of the present invention includes urolithin A or pharmaceutically acceptable salts and esters thereof, for example, includes, but is not limited to, urolithin A 3-formate, urolithin A 8-acetate, urolithin A 3,8-diacetate, urolithin A 8-propionate, urolithin A 8-butyrate, urolithin A 3,8-diisobutyrate, urolithin A 3,8-disalicylate, urolithin A 8-benzoate, urolithin A 8-citrate, urolithin A 8-stearate, urolithin A 3,8-palmitate, urolithin A 8-oleate, urolithin A 3,8-didodecanoate, preferably includes derivatives selected from the group of diacylated derivatives, most preferably the urolithin A derivative is urolithin A-8,3 diacetate. However, it will be apparent to those skilled in the art that other equivalent salts may be used with an expectation of success as demonstrated herein for specific forms of urolithin A.

The composition of the invention may conveniently be administered in the form of dosage units and may be prepared by any methods well known in the pharmaceutical art.

As used herein, the term "pharmaceutical composition" should mean a composition including at least one active ingredient and at least one ingredient which is not an active ingredient (e.g., not limited to, filler or dye) that makes the composition suitable for use in specific, effective recipients among mammals (for example, but not limited to, humans).

The term "active ingredient" as defined with regard to the term "pharmaceutical composition" should be understood to mean a component of the pharmaceutical composition that provides a primary pharmaceutical benefit, as opposed to an "inactive ingredient" which could be essentially recognized as not providing a pharmaceutical benefit.

It will also be understood by those skilled in the art that some of the compounds of the present invention may exist in a free form or, where appropriate, as a pharmaceutically acceptable derivative or prodrug thereof. In accordance with the present invention, a pharmaceutically acceptable derivative or prodrug includes, but is not limited to, pharmaceutically acceptable salts, esters, salts of such esters or any other addition compound or derivative that, when administered to a patient in need thereof, is able to provide, directly or indirectly, a compound as described herein or a metabolite, or a residue thereof.

The term "pharmaceutically acceptable salt" as used herein refers to those salts that are suitable for use in contact with tissues of human and lower animals without excessive toxicity, irritation, allergic response and the like, and are commensurate with a reasonable benefit/risk ratio. "Pharmaceutically acceptable salt" means any non-toxic salt or salt of an ester of the compound of the present invention that, when administered to a recipient, is able to provide, directly or indirectly, a compound of the present invention or an inhibiting metabolite or residue thereof.

The term prodrug as used herein is defined as a pharmacological substance that is administered in an inactive or less active form. After administration, it is converted in the patient's body into an active and effective form.

Dosage forms for topical or transdermal administration of the compound of the present invention include ointments, pastes, creams, lotions, gels, powders, solutions, sprays, or patches.

In addition, transdermal patches that have the added advantage of providing controlled delivery of the compound to the body are contemplated in the present invention. Such dosage forms are prepared by dissolving or dispensing the compound in the appropriate medium. Absorption enhancers can also be used to increase penetration of the compound through the skin. The rate can be controlled by using a rate controlling membrane or by dispersing the compound in a polymer matrix or gel.

Pharmaceutical compositions include, but are not limited to, pharmaceutical compositions containing at least one compound of the present invention and/or an acceptable salt or solvate thereof (e.g., pharmaceutically acceptable salt or solvate) as an active ingredient in combination with at least one carrier or auxiliary substance (e.g., pharmaceutical carrier or auxiliary substance) and may be used in treatment clinical conditions indicated in the present invention.

Urolithin A or a pharmaceutically acceptable salt or prodrug thereof, which is the active ingredient of the composition according to the invention, may be combined with a carrier in a liquid or semi-solid form during preparation of the dosage unit. The pharmaceutical carrier must be able to mix homogeneously with all ingredients of the composition and must be tolerated by an individual recipient. However, other physiologically active ingredients may also be included in the pharmaceutical composition of the invention, if desired, and when the ingredients are capable of being mixed homogeneously with the other ingredients of the composition. The pharmaceutical composition may be prepared by any suitable means, usually by uniformly intermixing the active compound(s) with liquids or a finely divided solid carrier, or both, in desired proportions, and then, if necessary, forming the resulting mixture into the desired shape.

The pharmaceutical composition of the invention may be in a liquid or semi-solid form.

The form of the pharmaceutical composition depends on the form in which the composition is prepared.

Semi-solid embodiments of the topical pharmaceutical composition of the present invention include, but are not limited to, ointments, creams, pastes, gels.

Liquid embodiments of the topical pharmaceutical composition of the present invention include, but are not limited to, tonics, balms, lotions, sprays, foams, solutions, emulsions, aqueous or oily suspensions.

Dosages and dosing frequency will be determined by a skilled in the art of medicine depending on the properties of a particular topical composition and on the type and severity of the dermatological disorder to be treated or prevented. The amount of pharmaceutical composition to be applied will depend on factors such as the particular compound, the application for which it is intended, the route of administration, and the condition of the patient being treated—all of these dosage parameters are within the range that can be determined by an ordinarily skilled artisan in medical science.

It should also be noted that the compounds and pharmaceutically acceptable compositions of the present invention can be used in combination therapies, i.e. the compounds and pharmaceutically acceptable compositions may be administered simultaneously, before or after one or more other desired therapeutic or medical treatments. The specific combination of therapies (treatment or procedures) to be used in the combined regimen will take into account the compatibility of the desired treatment and/or procedures and desired therapeutic effect to be achieved. It should also be noted that the therapies used may allow the desired effect for the same disorder to be achieved (for example, a compound of the invention may be administered concurrently with another agent used to treat the same disorder), or may allow different effects to be achieved (e.g., combating any harmful effects). Additional therapeutic agents used herein, which are usually administered in the treatment or prophylaxis of a particular disease or condition, are known as "appropriate for the disease or condition being treated."

The amount of additional therapeutic agent present in the compositions of the present invention will be no more than the amount that would normally be administered in a composition containing that therapeutic agent as the only active agent.

In general, the compound described above is present in the formulation of the invention in an amount from about 0.0001 weight percent to about 15 weight percent based on the total weight of the composition, preferably from about 0.01 weight percent to about 5 weight percent based on the total weight of the composition, most preferably from about 0.1 weight percent to about 2 weight percent based on the total weight of the composition.

In order to treat inflammations of skin and mucous membranes, the topical composition of the present invention is topically applied directly to the diseased area in any conventional manner well known in the art, for example, using a dropper or application stick, in the form of a mist using a spray applicator, by intradermal or transdermal patch or by simple mechanical spreading the composition of the invention on the diseased area.

Generally, the amount of the composition for topical administration applied to the diseased area ranges from about 0.0001 g/cm² of skin surface area to about 0.5 g/cm², preferably 0.001 g/cm² to about 0.2 g/cm² of skin surface area. Usually, application in the amount of 0.005 to 0.1 g/cm² daily for the duration of treatment is recommended, administered one or more times a day, in single or multiple doses.

SHORT DESCRIPTION OF FIGURES

FIG. 1 shows changes in ear thickness caused by induced inflammation (by DNCB) followed by local treatment with 0.2 and 1.0% urolithin or its white petrolatum carrier. The positive control group were rats treated with 1% hydrocortisone composition. The negative control group were rats without induced inflammation. The symbols used in post-hoc comparisons mean: #—Petrolatum vs. Negative control; †—1% Hydrocortisone vs. Negative control; &—0.2% Urolithin A vs. Negative control; γ—1.0% Urolithin A vs. Negative control; χ—1% Hydrocortisone vs. Petrolatum; *—0.2% Urolithin A vs. Petrolatum; Φ—0.2% Urolithin A vs. Petrolatum; Ω—1.0% Urolithin A vs. 1% Hydrocortisone. One, two or three symbols indicate the significance of comparisons at the level of $p<0.05$, $p<0.01$, $p<0.001$, respectively.

FIG. 2 shows changes in the frequency of scratch reflexes caused by induced inflammation (by DNCB) followed by local treatment with urolithin at a dose of 0.2 and 1.0% or its white petrolatum carrier. The positive control group were rats treated with 1% hydrocortisone composition. The negative control group were rats without induced inflammation. The symbols used in post-hoc comparisons mean: #—Petrolatum vs. Negative control; χ—1% Hydrocortisone vs. Negative control; &—0.2% Urolithin A vs. Negative control; γ—1.0% Urolithin A vs. Negative control; χ—1% Hydrocortisone vs. Petrolatum; *—0.2% Urolithin A vs. Petrolatum; Φ—0.2% Urolithin A vs. Petrolatum; Ω—1.0% Urolithin A vs. 1% Hydrocortisone. One, two or three symbols indicate the significance of comparisons at the level of $p<0.05$, $p<0.01$, $p<0.001$, respectively.

FIG. 3 shows the total number of leukocytes [$n/1\times10^9$] and their percentage in rats of the negative control group (without induced inflammation), the relevant control group (with induced atopic dermatitis, exposed to petroleum), the positive control group (with induced atopic dermatitis, exposed to 1% hydrocortisone) and groups of rats with induced atopic dermatitis, exposed to the active compounds tested (0.2 and 1.0% urolithin A). The symbols used in post-hoc comparisons mean: #—Petrolatum vs. Negative control; †—1% Hydrocortisone vs. Negative control; &—0.2% Urolithin A vs. Negative control; γ—1.0% Urolithin A vs. Negative control; *—0.2% Urolithin A vs. Petrolatum; Φ—0.2% Urolithin A vs. Petrolatum. One, two or three symbols indicate the significance of comparisons at the level of $p<0.05$, $p<0.01$, $p<0.001$, respectively.

FIG. 4 shows the total number of monocytes [$n/1\times10^9$] and their percentage in rats of the negative control group (without induced inflammation), the relevant control group (with induced atopic dermatitis, exposed to petroleum), the positive control group (with induced atopic dermatitis, exposed to 1% hydrocortisone) and groups of rats with induced atopic dermatitis, exposed to the active compounds tested (0.2 and 1.0% urolithin). The symbols used in post-hoc comparisons mean: #—Petrolatum vs. Negative control; †—1% Hydrocortisone vs. Negative control; &—0.2% Urolithin A vs. Negative control; γ—1.0% Urolithin A vs. Negative control; *—0.2% Urolithin A vs. Petrolatum; Φ—0.2% Urolithin A vs. Petrolatum. One, two or three symbols indicate the significance of comparisons at the level of $p<0.05$, $p<0.01$, $p<0.001$, respectively.

FIG. 5 shows the total number of neutrophils [$n/1\times10^9$] and their percentage in rats of the negative control group (without induced inflammation), the relevant control group (with induced atopic dermatitis, exposed to petroleum), the positive control group (with induced atopic dermatitis, exposed to 1% hydrocortisone) and groups of rats with induced atopic dermatitis, exposed to the active compounds tested (0.2 and 1.0% urolithin). The symbols used in post-hoc comparisons mean: #—Petrolatum vs. Negative control; †—1% Hydrocortisone vs. Negative control; &—0.2% Urolithin A vs. Negative control; γ—1.0% Urolithin A vs. Negative control; *—0.2% Urolithin A vs. Petrolatum; Φ—0.2% Urolithin A vs. Petrolatum. One, two or three symbols indicate the significance of comparisons at the level of p<0.05, p<0.01, p<0.001, respectively.

FIG. 6 shows the total number of lymphocytes [n/1×10$^9$] and their percentage in rats of the negative control group (without induced inflammation), the relevant control group (with induced atopic dermatitis, exposed to petroleum), the positive control group (with induced atopic dermatitis, exposed to 1% hydrocortisone) and groups of rats with induced atopic dermatitis, exposed to the active compounds tested (0.2 and 1.0% urolithin). The symbols used in post-hoc comparisons mean: #—Petrolatum vs. Negative control; †—1% Hydrocortisone vs. Negative control; &—0.2% Urolithin A vs. Negative control; γ—1.0% Urolithin A vs. Negative control; *—0.2% Urolithin A vs. Petrolatum; Φ—0.2% Urolithin A vs. Petrolatum. One, two or three symbols indicate the significance of comparisons at the level of p<0.05, p<0.01, p<0.001, respectively.

FIG. 7 The plot showing the effect of urolithin A (UA), urolithin B (UB) and iso-urolithin A (iUA) on the extracellular level of S100A8/A9 protein. Urolithins were incubated at three concentrations (40, 10 and 1 μM) with neutrophils isolated from human peripheral blood. Statistical significance: **—p<0.001 versus stimulated control (Dunnett's test); #—statistical significance (p<0.001) versus unstimulated control; ST—stimulated control; NST—unstimulated control.

FIG. 8 shows the histology of skin lesions in rats in the atopic dermatitis model—lesions treated with the composition of urolithin A. Mild epidermal hyperplasia, infiltration of mononuclear cells (mast cells) and neutrophils. A slight infiltration of inflammatory cells around the blood vessels.

Figure 12:
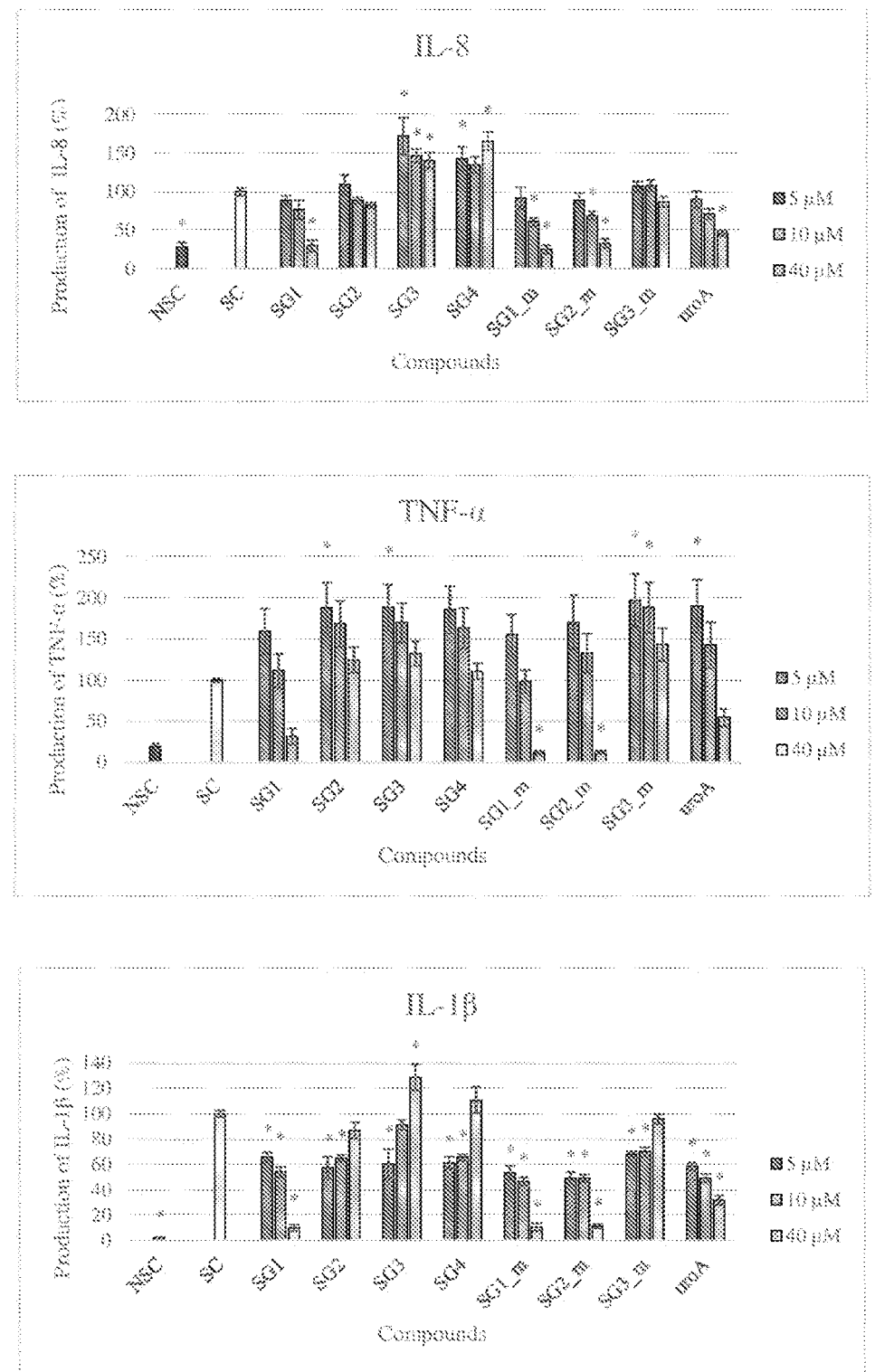

FIG. 12 shows plots indicating the effect of urolithin A (UA) and its acylated derivatives (SG1, SG2, SG3, SG4, SG1_m, SG2_m, SG3_m) on the production of IL-8, TNF-alpha and IL-1beta by neutrophils isolated from human peripheral blood. Urolithin A and its acylated derivatives were incubated with neutrophils at 5, 10 and 40 μM, then cells were stimulated with LPS at 100 ng/mL for 24 h. Statistical significance: *—p<0.001 versus stimulated control (Dunnett's test). SC—stimulated control, NSC—unstimulated control.

Figure 13:
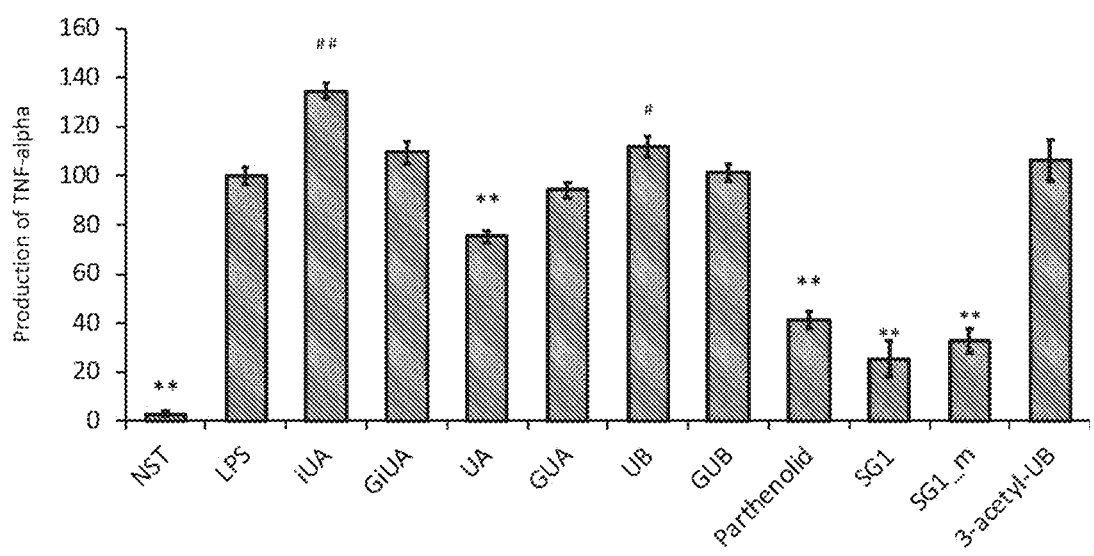

FIG. 13 shows a plot indicating the effect of iso-urolithin A (iUA), urolithin A (UA), urolithin B (UB), their respective glucuronides (GiUA, GUA, GUB), acetylated derivatives of urolithin A (SG1 and SG1_mono) and 3-acetyl-urolithin B on secretion of TNF-alpha by macrophages obtained from the THP-1 cell line. Urolithins and their derivatives were incubated with macrophages at a concentration of 40 μM. Parthenolide at a concentration of 5 μM was used as a positive control. Statistical significance: statistically significant decrease *—p<0.05, **—p<0.001 versus stimulated control (Dunnett's test); statistically significant increase #—p<0.05, ##—p<0.001 versus stimulated control (Dunnett's test).

Figure 14:
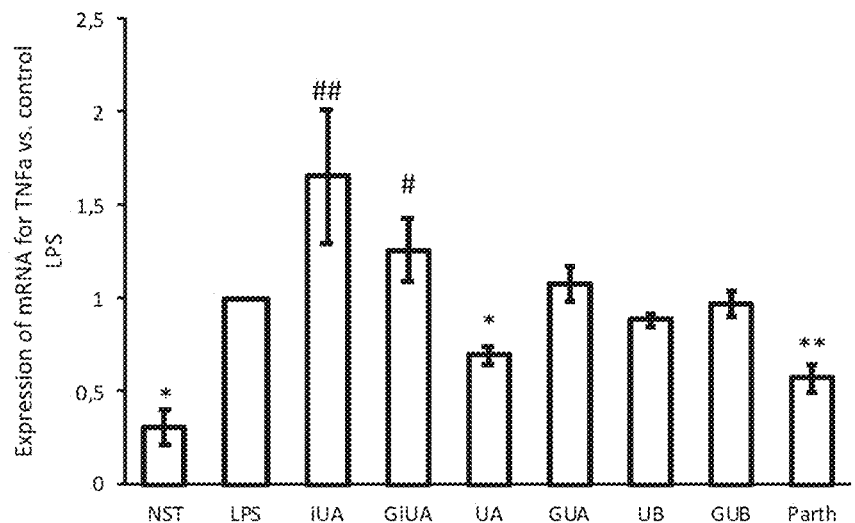

FIG. 14 shows a plot indicating the effect of iso-urolithin A (iUA), urolithin A (UA), urolithin B (UB), their respective glucuronides (GiUA, GUA, GUB) on expression of mRNA for TNF-alpha by macrophages obtained from the THP-1 cell line. Urolithins and their derivatives were incubated with macrophages at a concentration of 40 μM, then the cells were stimulated with LPS at a concentration of 100 ng/mL for 6 h. Parthenolide at a concentration of 5 μM was used as a positive control. Statistical significance: statistically significant decrease *—p<0.05, **—p<0.001 versus stimulated control (Dunnett's test); statistically significant increase #—p<0.05, ##—p<0.001 versus stimulated control (Dunnett's test).

Figure 15:
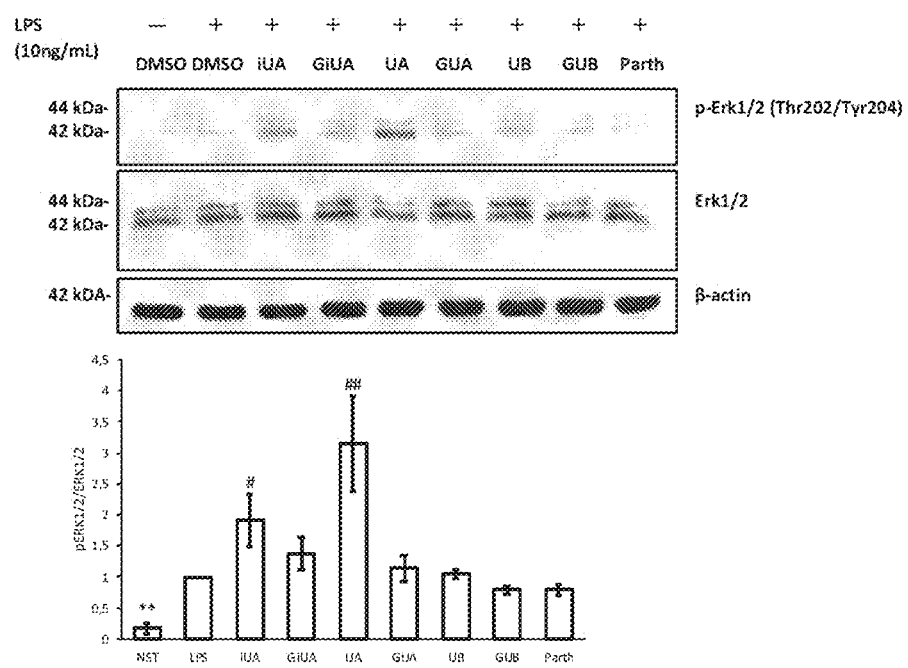

FIG. 15 shows a plot indicating the effect of iso-urolithin A (iUA), urolithin A (UA), urolithin B (UB), their respective glucuronides (GiUA, GUA, GUB) on ERK1/2 phosphorylation in macrophages obtained from the THP-1 cell line. Urolithins and their derivatives were incubated with macrophages at a concentration of 40 μM, then the cells were stimulated with LPS at a concentration of 10 ng/mL for 35 min. Parthenolide at a concentration of 5 μM was used as a positive control. Statistical significance: statistically significant decrease *—p<0.05, **—p<0.001 versus stimulated control (Dunnett's test); statistically significant increase #—p<0.05, ##—p<0.001 versus stimulated control (Dunnett's test).

Figure 16:
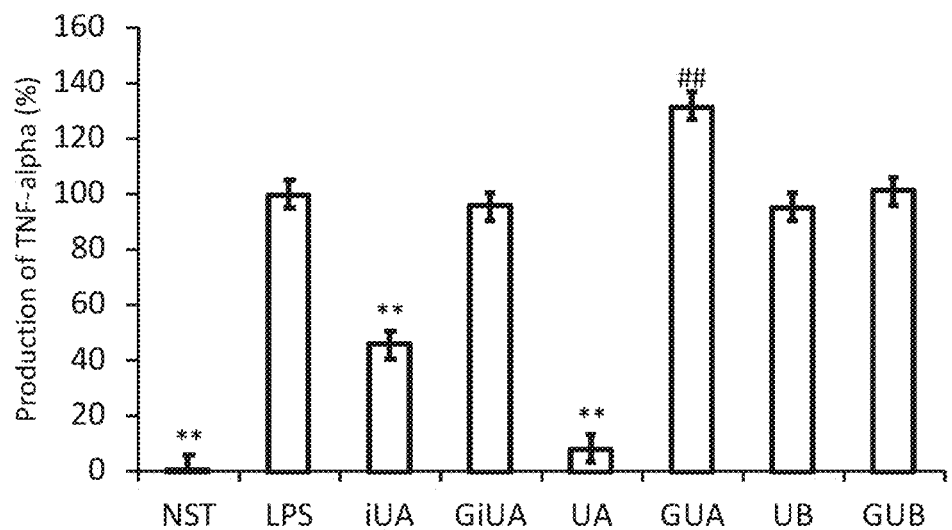

FIG. 16 shows a plot indicating the effect of iso-urolithin A (iUA), urolithin A (UA), urolithin B (UB), their respective glucuronides (GiUA, GUA, GUB) on TNF-alpha secretion by macrophages obtained from monocytes isolated from human peripheral blood. Urolithins and their derivatives were incubated with macrophages at a concentration of 40 μM, then the cells were stimulated with LPS at a concentration of 100 ng/mL for 24h. Statistical significance: statistically significant decrease *—p<0.05, **—p<0.001 versus stimulated control (Dunnett's test); statistically significant increase #—p<0.05, ##—p<0.001 versus stimulated control (Dunnett's test).

Figure 17:
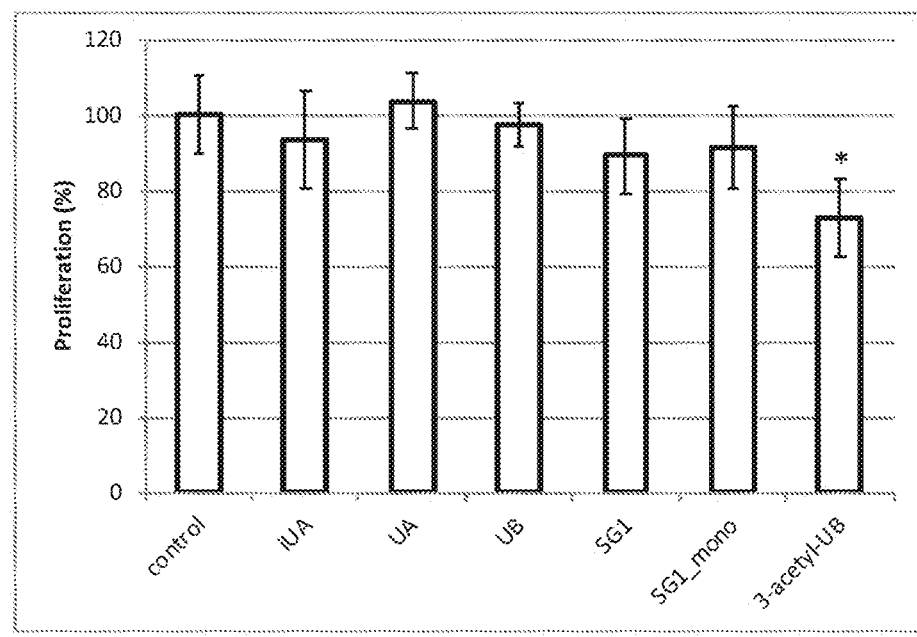

FIG. 17 shows a plot indicating the effect of urolithin A (UA), urolithin B (UB) and iso-urolithin A (iUA), acetylated derivatives of urolithin A (SG1 and SG1_mono) and 3-acetyl-urolithin B on proliferation of human skin fibroblasts. Urolithins were incubated at a concentration of 40 μM with human fibroblast cells. Statistical significance: **—p<0.001 versus control (Dunnett's test).

Figure 18:
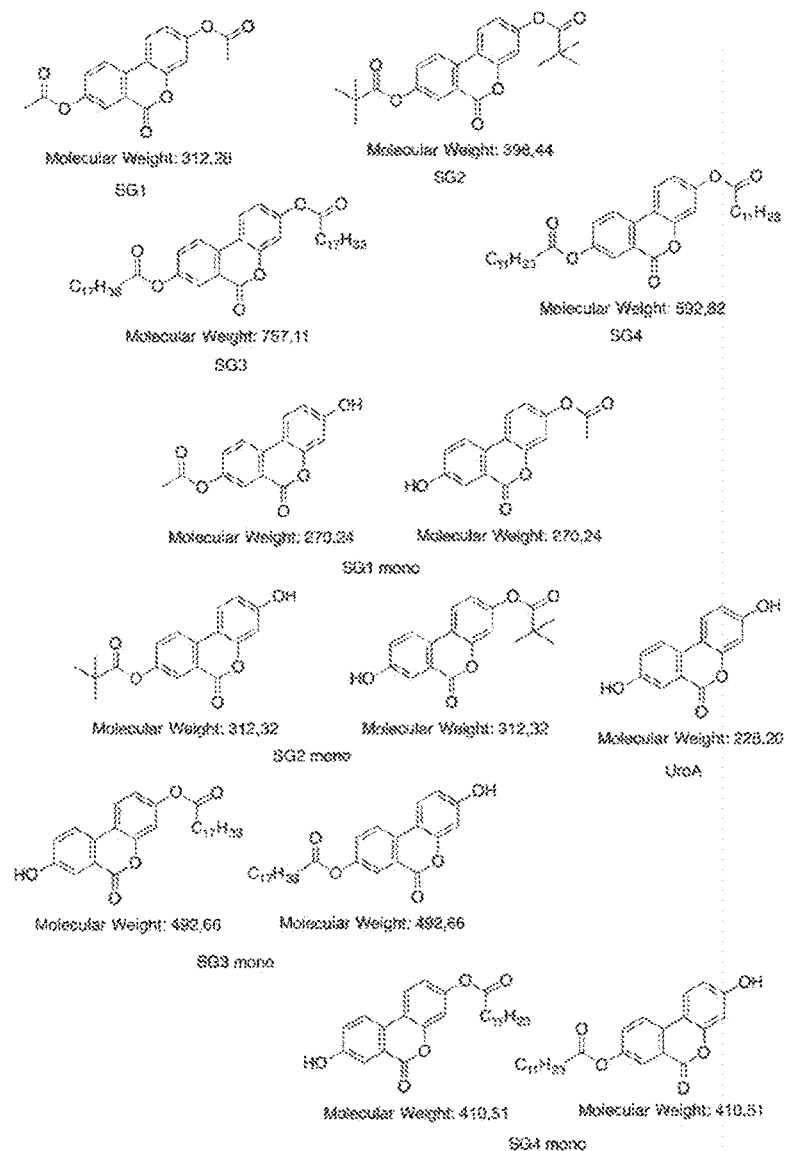

FIG. 18 shows the structures of acyl derivatives of urolithin A tested—SG1, SG2, SG3, SG4, SG1_m, SG2_m, SG3_m.

Figure 19:
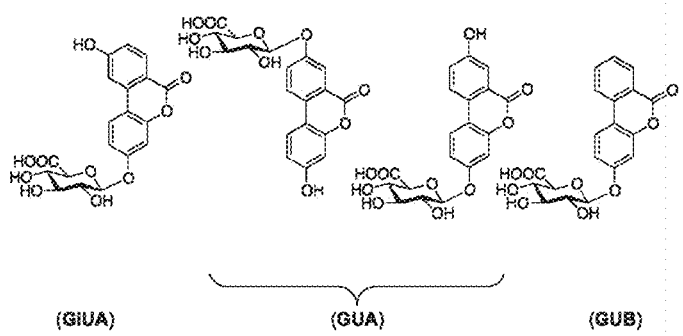

FIG. 19 shows the structures of urolithin glucuronides tested. Iso-urolithin A 3-O-glucuronide (GiUA), a mixture of urolitin A 3-O-glucuronide and urolitin A 8-O-glucuronide (GUA), urolitin B 3-O-glucuronide (GUB).

RESEARCH METHODOLOGY

In Vivo Evaluation of Urolithin a Effectiveness in the Treatment of Atopic Dermatitis in a Rat Model Materials and Methods The animal model in which urolithin A activity has been demonstrated may be referred to any inflammatory skin disorders. It is similar to the indications for use of hydrocortisone, which was used as a positive control in the study.

Urolitin A was obtained by synthesis according to Bialonska et al. (Bialonska et al., 2009) or purchased from Sigma-Aldrich. The ointment containing urolithin A was prepared by emulsifying the weighed substance into a solid vehicle (white petrolatum) using an unguator.

Wistar rats aged 5-6 weeks (at the start of the experiment) kept under standard conditions with free access to feed and water were used for the tests. The animals were divided into 5 groups, 8 individuals in each group. To prepare 2,4-dinitrochlorobenzene (DNCB) composition inducing inflammation, DNCB was dissolved in 70% ethanol to a final concentration of 1.5% (w/v). Therapeutic composition was an ointment based on white petrolatum with 0.2% or 1.0% urolithin A added. The control ointment was white petrolatum without addition of urolithin A.

The induction of chronic atopic dermatitis involved local 9-fold infiltration with 60 µl 1.5% 2,4-dinitrochlorobenzene (DNCB) on each (external and internal) surface of the right ear over 3 weeks (3 times a week). Negative control was the right ear of rats without induction inflammation.

Treatment of atopic dermatitis with 0.2% or 1.0% urolithin composition and white petrolatum (control) or 1.0% hydrocortisone composition (positive control) was started eight days after sensitization—one day before the fourth application of DNCB. Ointments with appropriate for given group drug added were applied in a total volume of about 20 µl to each ear surface one day before and 6 hours after each DNCB application (for a period of 3 weeks). The negative control group consisted of rats without induced inflammation and treated with white petrolatum in a regimen analogous to the composition of urolithin A or hydrocortisone.

Evaluation Effectiveness of the Composition

Measurement of Ear Thickness.

Ear thickness was assessed using an electronic mini caliper the day before inflammation was induced (day 0) and then on days 4 and 8 prior to treatment and on days 4, 8, 12, 16, 22 and 26 of therapy with urolithin A composition (on days 12, 16, 20, 24, 28 and 32 after inflammation inducing, respectively).

Measurement of Pruritus Level.

Measurement of pruritus level (as measured by scratching reflexes) was evaluated as the total frequency of scratch reflexes during 10 minutes immediately after DNCB application on days 0, 4, 8, 12, 16, 20, 24, 28 and 32 of the experiment). Scratching was defined as a single or series of several reflexes of scratching with a paw directed at the site of DNCB application.

Peripheral Blood Morphology.

2 mL blood samples were drawn into syringes (containing heparin as an anticoagulant) from the heart under general anesthesia (isoflurane) on day 32 of the experiment. The test was conducted using the DIATRON automated hematology analyzer. Peripheral blood analysis included the assessment of morphotic elements in blood: erythrocytes, leukocytes and thrombocytes and determination of the number and percentage of different types of leukocytes—WBC as well as values of erythrocyte indicators: hemoglobin (HGB), hematocrit (HCT), mean corpuscular volume (MCV), mean corpuscular hemoglobin (MCH) and mean corpuscular hemoglobin concentration (MCHC).

Histologic Assessment

Histologic assessment was performed on the skin of the ears of rats with induced inflammation and on the skin of the ears of control rats taken on day 32 of the experiment. The evaluation was performed on 20 µm skin sections stained with standard hematoxylin/eosin (H&E) to assess inflammatory cell infiltration, and with toluidine blue to assess the presence of mast cells.

Statistical Analysis

The experimental results obtained were analyzed using the Statistica 7.1 program (StatSoft, Inc., Tulsa, OK, USA) and presented as mean values±SE. Statistical significance was set at P≤0.05. The results with established normal distribution in the D'Agostin and Pearson test were prepared using two- or three-factor analysis of variance (ANOVA). Parametric post-hoc analysis for individual time points was performed using the Bonferroni test.

Results

DNCB-Induced Local (Swelling and Hyperemia of the Ear) and Systemic (Changes in Blood Morphology) Inflammatory Changes:

Local Changes.

Figure 1:
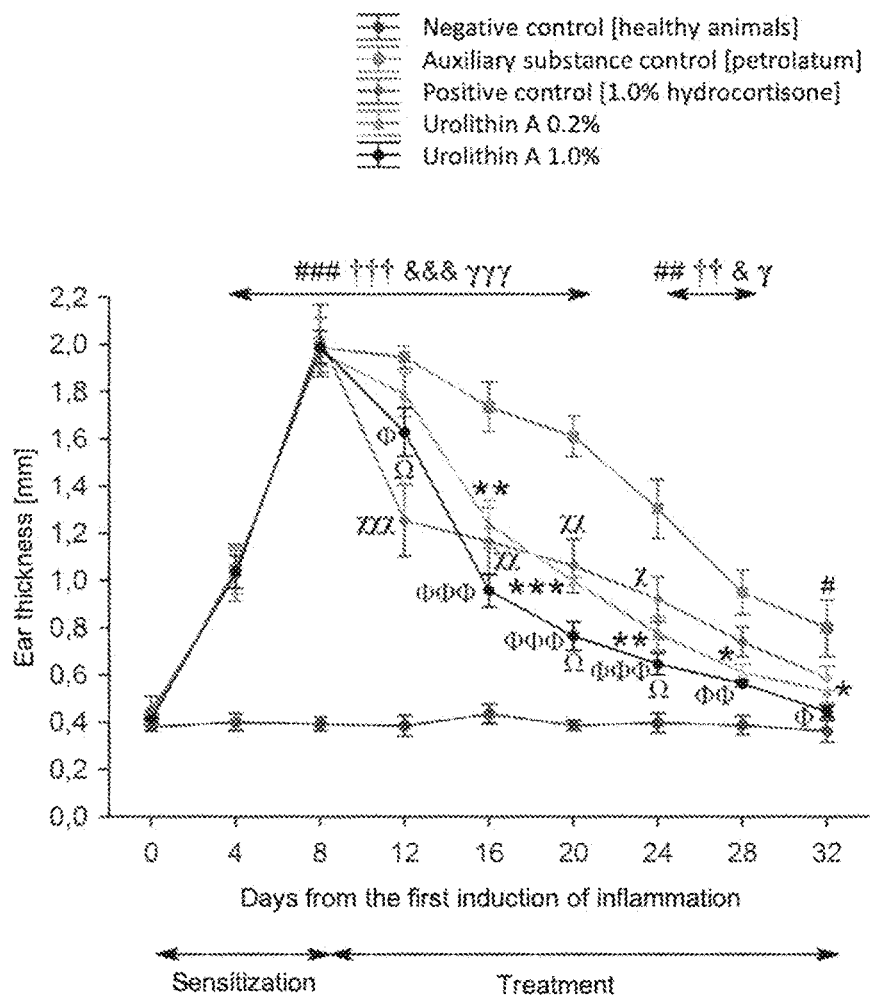

Analysis using 2-factor analysis of variance (ANOVA) showed that the 8-day period of sensitization of the ear skin using 1.5% DNCB caused inflammation manifested as significant [p<0.001–the main effect of DNCB] and rapid [p<0.001–DNCB interaction×Time] edema and redness of the ear auricle (FIG. 1).

Scratching.

Behavioral assessment revealed scratching reflexes in response to DNCB-induced inflammation from day 4 of induction of inflammation (p<0.05). 2-factor ANOVA performed for the entire induction period of inflammation showed that this effect was similar in all groups prior the treatment started (up to day 8) with respect to both intensity and increase in reflex frequency over the sensitization period studied.

Effect of Topical Therapy with Urolithin-A on DNCB-Induced Inflammatory Changes:

Inhibition of Local Changes.

Ear edema, used as a parameter of atopic dermatitis, was reduced after the introduction of the local therapy with both urolithin A [p<0.001] and hydrocortisone [p<0.01](FIG. 1), with the analysis using 2-factor ANOVA showing that the effect was stronger when urolithin was used [F (1.28)=6.16; p<0.05]. A significant effect was also found for the applied urolithin dose, which was more effective at a concentration of 1% [p<0.05–comparison of urolithin doses with each other]. Analysis of variance performed separately for each urolithin dose also showed that a significantly greater anti-inflammatory effect compared to hydrocortisone was obtained only at a concentration of 1% [p<0.05–Urolitin A 1% vs. Hydrocortisone 1%] in the absence of significantly greater efficiency at a dose of 0.2% [Urolitin A 0.2% vs. Hydrocortisone 1%].

Significant interaction effect: the anti-inflammatory compound tested (urolithin A vs. hydrocortisone)×time indicates a different time profile of the anti-inflammatory effect of the compositions tested, characterized by a greater therapeutic effectiveness of hydrocortisone in the initial period of therapy (up to 12 days) compared to urolithin, which was more effective in the later treatment period [p<0.01](from day 12 to 28 of treatment) both at the dose of 0.2 and 1%. A gradual decrease of edema was also found when using petrolatum as a carrier of active substances [p<0.01–main effect of time), however this effect was significantly weaker compared to when the active substances were used.

Antipruritic Efficacy (Scratching).

Figure 2:
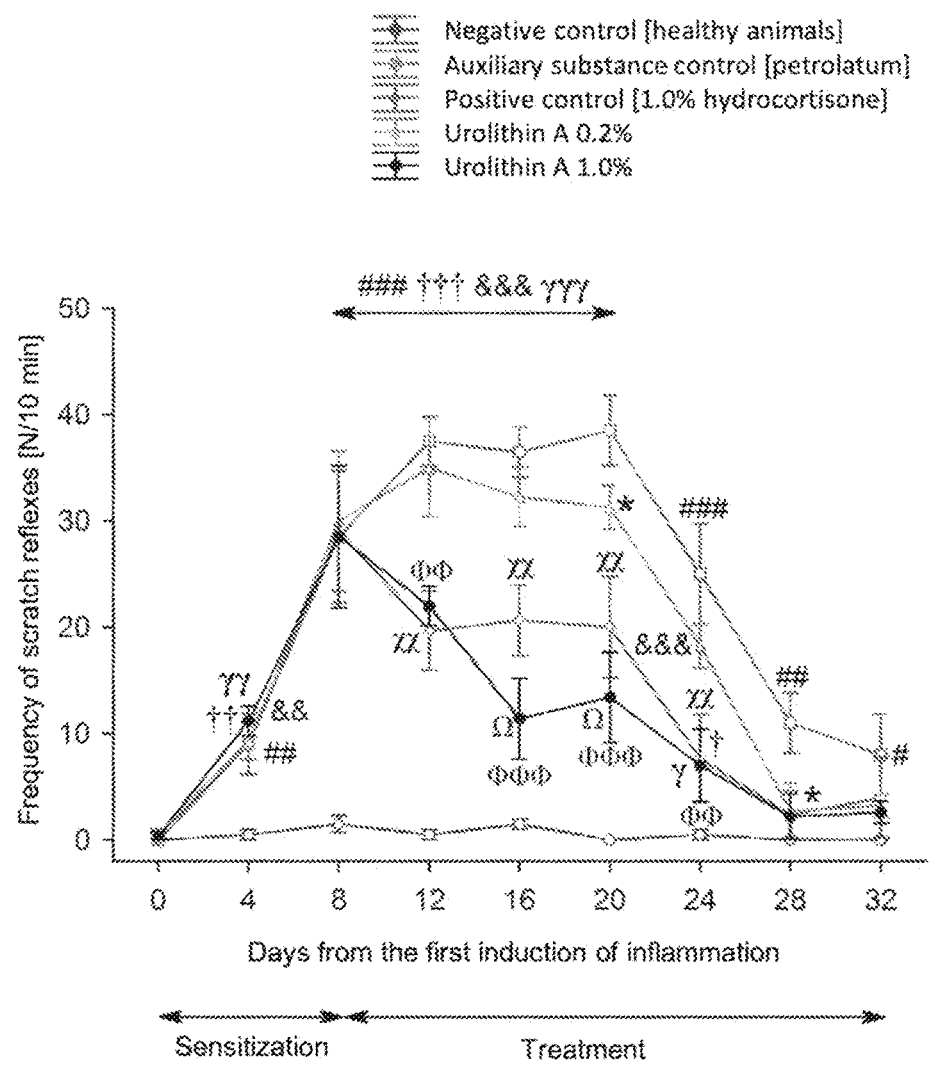
Figure 3:
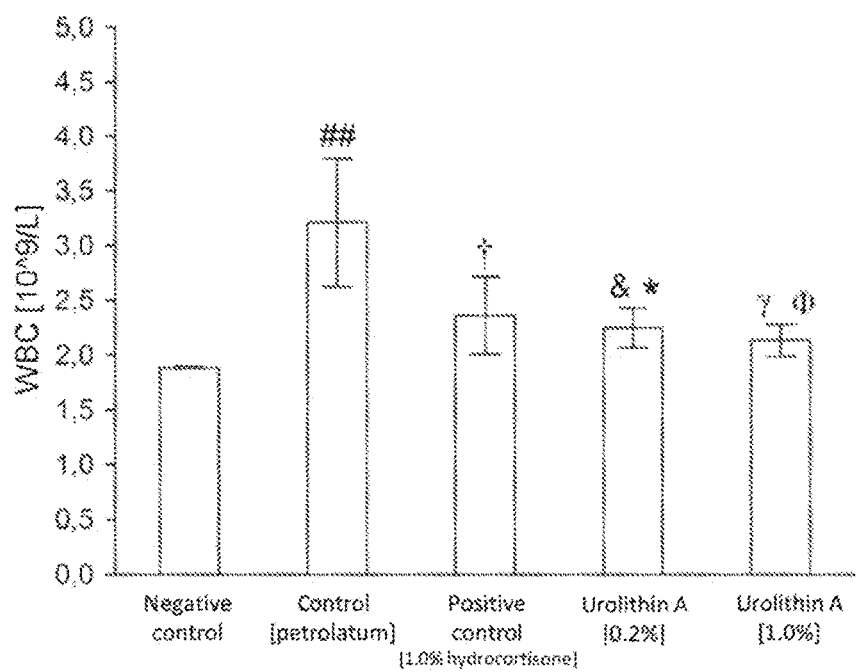
Figure 4:
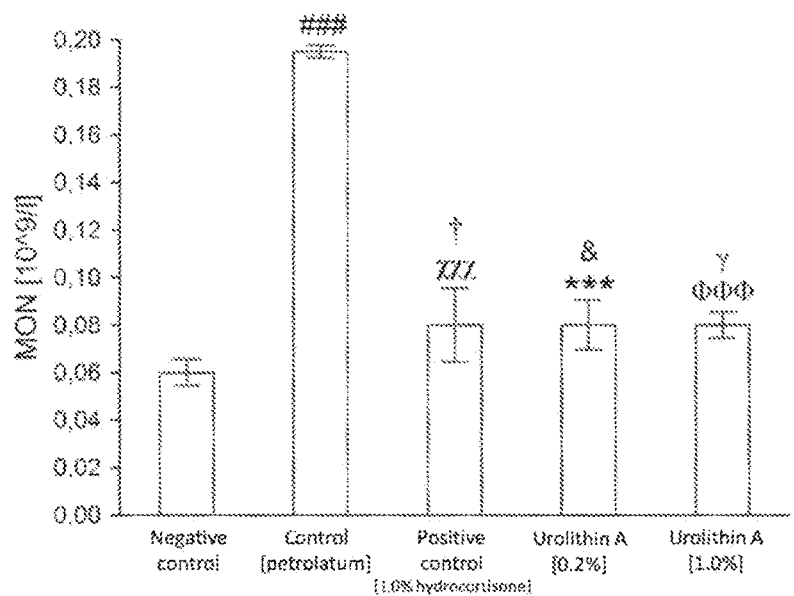
Figure 4:
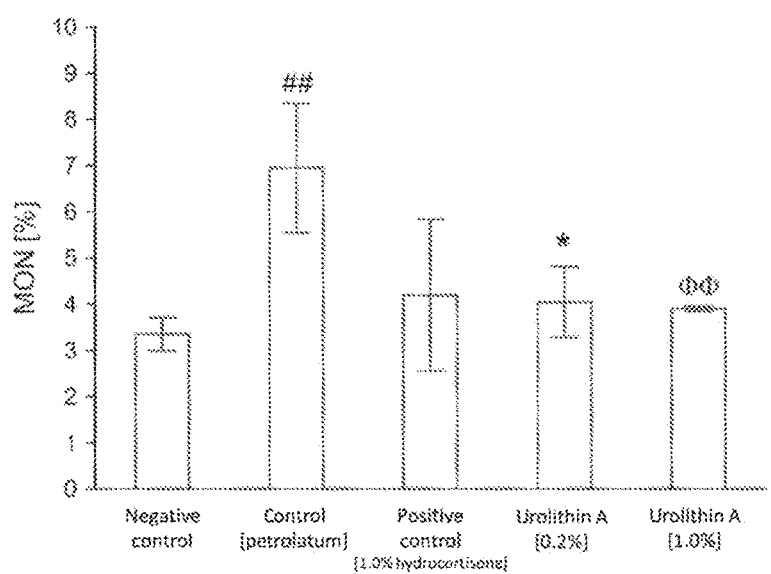
Figure 5:
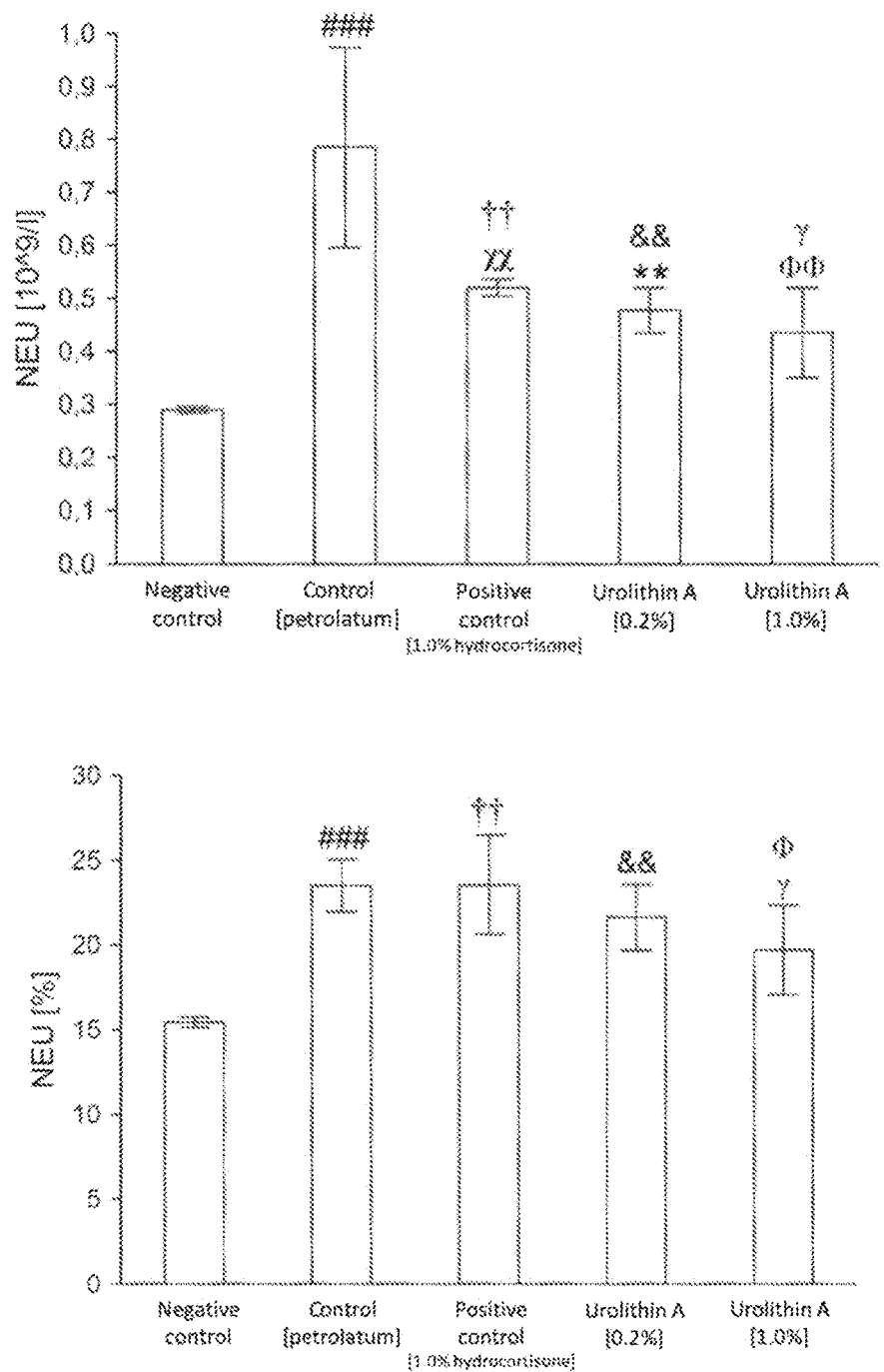
Figure 6:
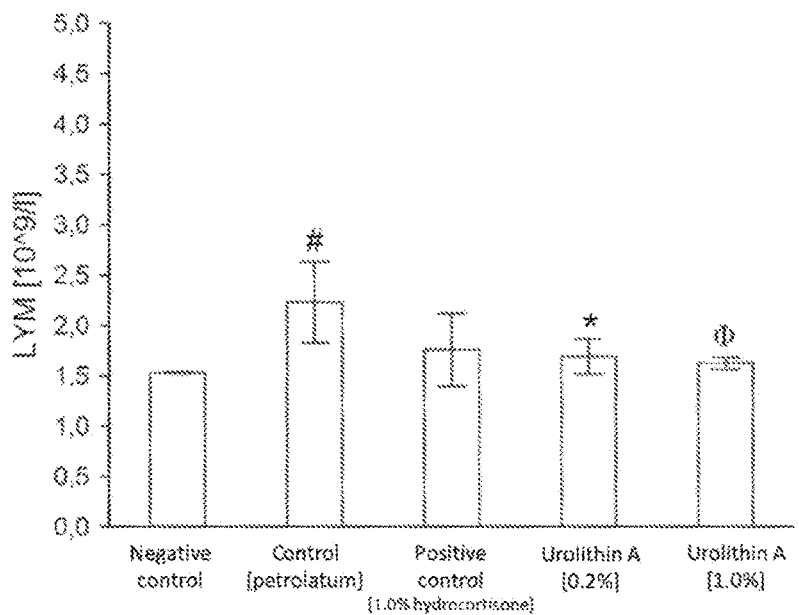
Figure 6:
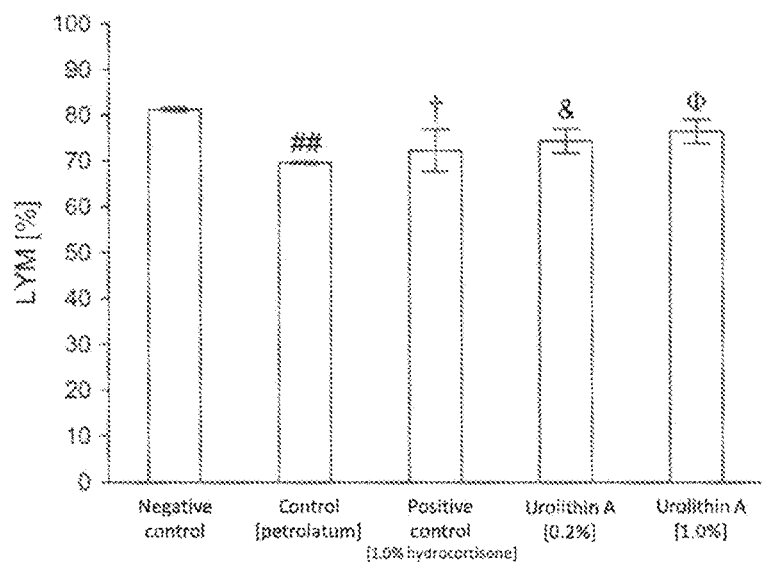
Figure 7:
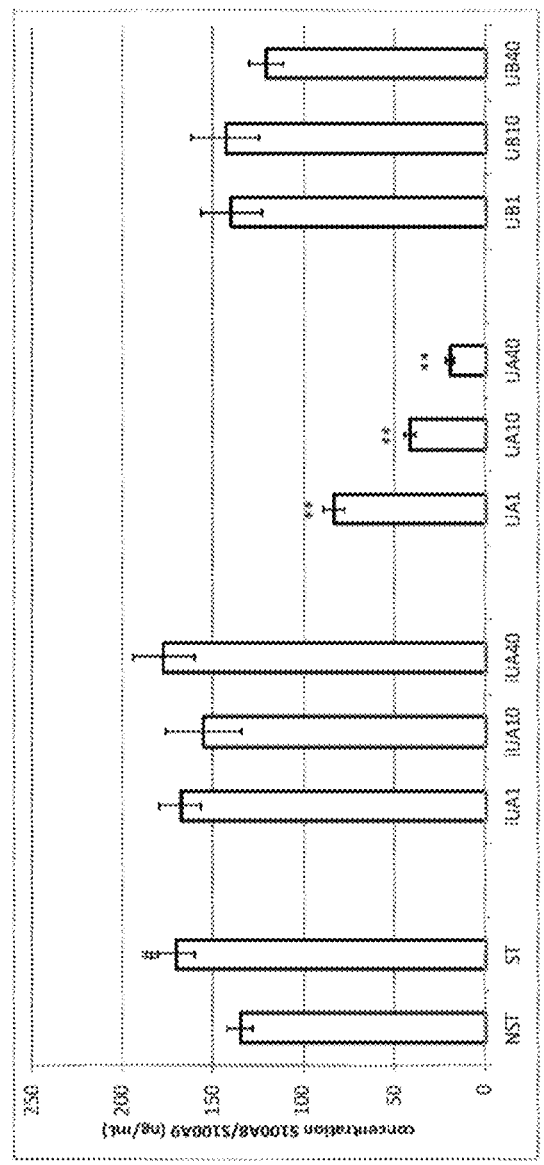
Figure 8:
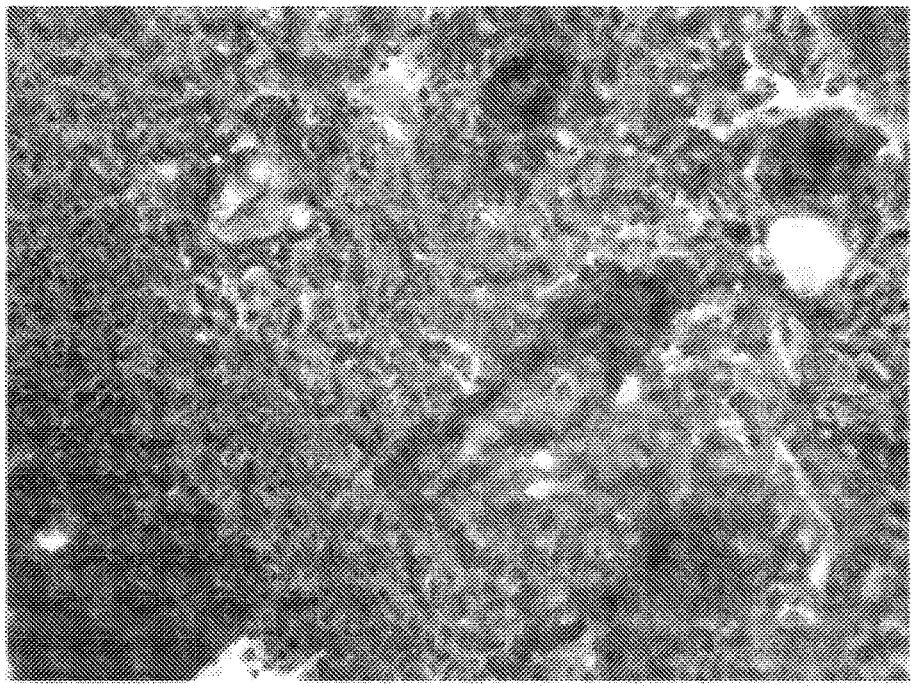
Figure 8:
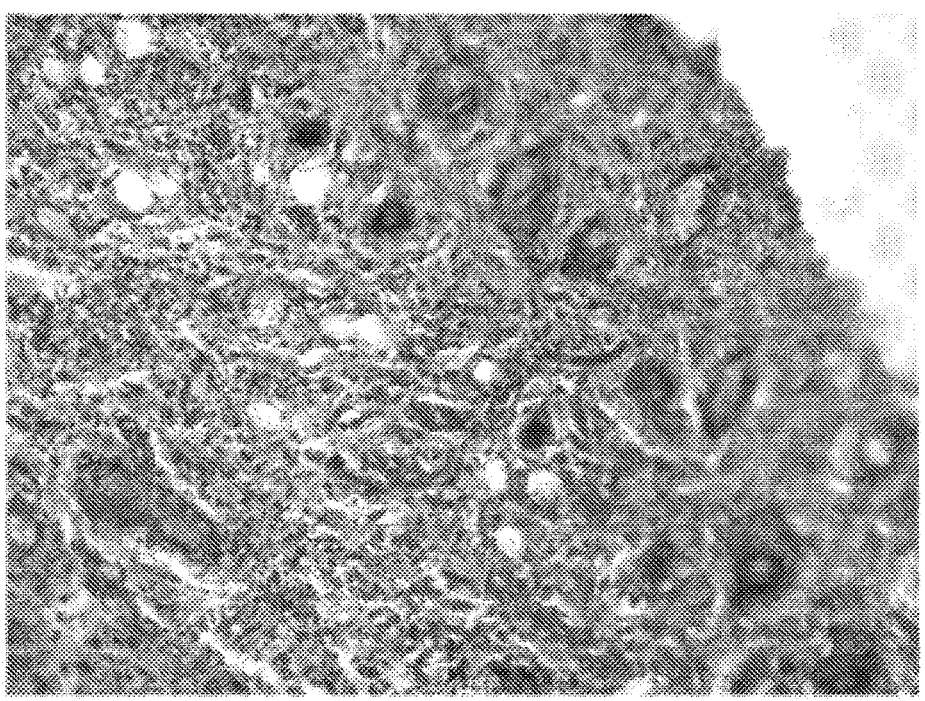
Figure 9:
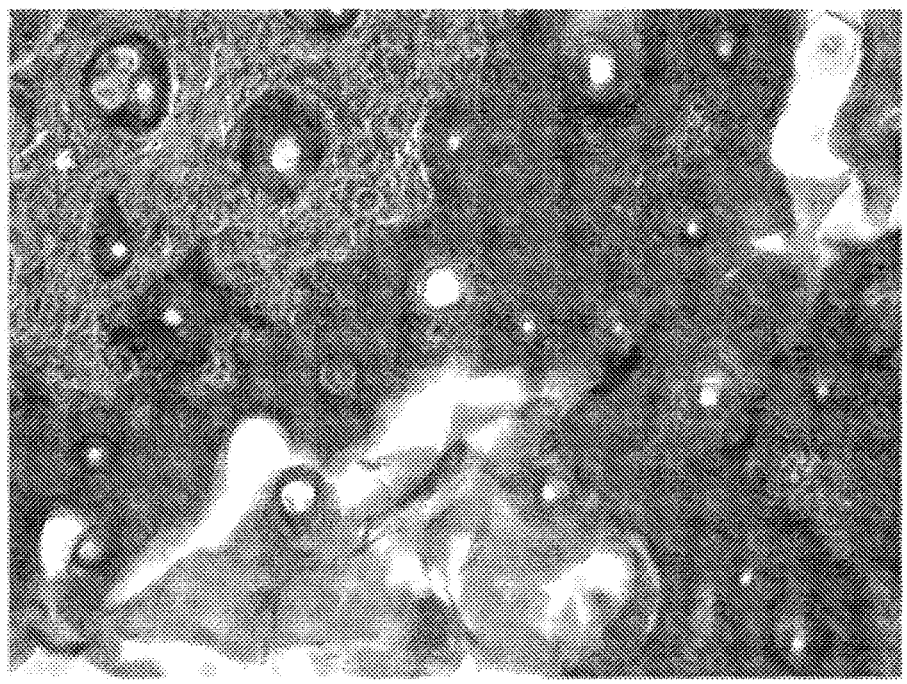
FIG. 9 shows the histology of skin lesions of rats in the atopic dermatitis model—lesions treated with petrolatum. Significant epidermal hyperplasia, epidermal hyperkeratosis, infiltration of mononuclear cells (mast cells).
Figure 10:
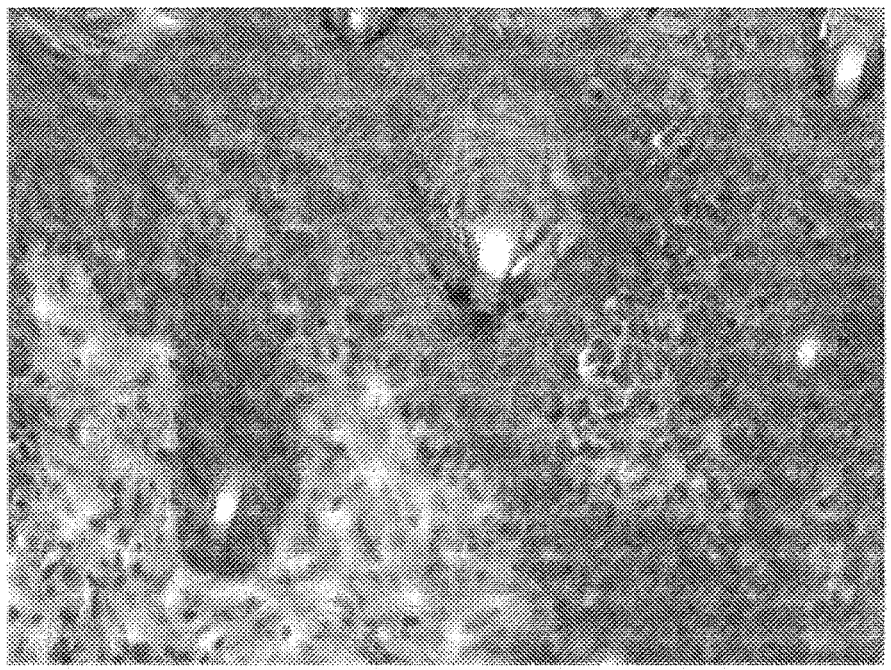
FIG. 10 shows the histology of skin lesions of rats in the atopic dermatitis model—lesions treated with petrolatum. Epidermal spongiosis being the result of the separation of unchanged keratinocytes by effusion accumulating between cells.
Figure 11:
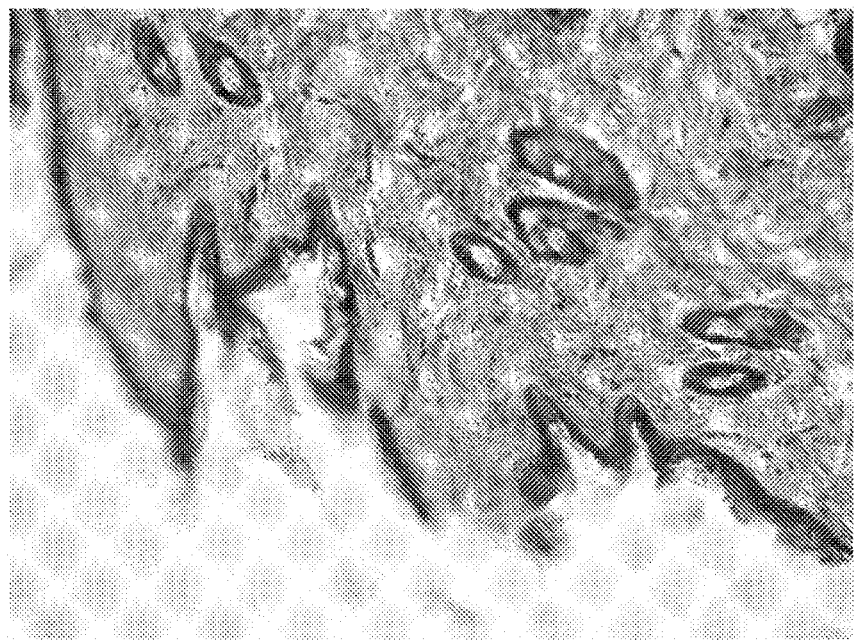
FIG. 11 shows normal histology of the skin in a rat without induced atopic dermatitis.

Behavioral assessment showed a reduction in scratching rate with both urolithin A [p<0.001] and hydrocortisone [p<0.01] used, with the effect being stronger compared to urolithin [p<0.05–effect](FIG. 2). The greater effect of inhibition of scratching reflexes by urolithin is determined by the use of an appropriate dose of urolithin, which was more effective at a concentration of 1% [p<0.05–comparison of urolithin doses with each other]. Analysis of variance performed separately for each dose of urolithin also showed that a significantly greater inhibition of scratching reflexes compared to hydrocortisone was obtained only at a concentration of 1% [p<0.05–Urolithin A 1% vs. Hydrocortisone 1%] in the absence of significantly greater efficiency at a dose of 0.2% [p=0.39–Urolithin A 0.2% vs. Hydrocortisone 1%]. The lack of significance of the interaction effect in respect to changes in the frequency of scratch reflexes in the studied time interval depending on the anti-inflammatory composition tested (interaction: urolithin A vs. hydrocortisone×time] indicates that, in contrast to the increased anti-edema effectiveness of hydrocortisone in the initial period of therapy (up to day 12) compared to urolithin, this effect was not found in relation to the inhibition of scratching reflexes. A gradual decrease in scratching reflexes was also found after the use of petrolatum as a carrier of active substances [p<0.01–main effect of time], but the effect was significantly weaker compared to the active substances used.

Changes in Blood Morphology Due to Atopic Dermatitis and Treatment with Anti-Inflammatory Compositions: White Blood Cell System.

The higher level of leukocytes in control rats treated with DNCB was mainly caused by an increase in the total monocyte count (with exceeding the norms prescribed for the rat) and neutrophils (with maintaining the norms prescribed for the rat), and consequently an increase in their percentage in the overall WBC parameter. The group of rats with induced inflammation and treated with white petrolatum as an urolithin A carrier was also characterized by an overall increase in lymphocyte count in the total leukocyte pool, however, due to the increase in monocyte and neutrophil counts, their percentage was lower than in the control rats. Undertaking treatment with 1% hydrocortisone as a positive control resulted in a significant reduction in WBC (p<0.05).

A decrease in the WBC level was also obtained with the tested urolithin A composition, which at an active substance concentration of 0.2% reduced WBC values similar to 1% hydrocortisone [p<0.05], while at a concentration of 1% at p<0.01. However, the higher level of significance of the effect obtained with 1% urolithin did not result in a significantly greater effect of WBC growth inhibition by this composition compared to 1% hydrocortisone. It should be noted that inhibition of growth in the WBC level by both 1% hydrocortisone and the tested composition of urolithin A at both concentrations used, i.e. 0.2 and 1%, was not fully effective. Final WBC values remained at a higher level compared to negative control groups of rats (without inducing atopic dermatitis).

As mentioned above, the increase in the WBC level induced by atopic dermatitis was conditioned by an increase in the population of monocytes, neutrophils and lymphocytes. However, inhibition of this process by hydrocortisone was only by reducing the population of monocytes and neutrophils, whereas due to a large variation in lymphocyte levels in the group treated with this control composition, there were no significant differences in their level as compared to the control group treated with petrolatum. Compared with the 1% hydrocortisone composition, urolithin A used at both concentrations significantly inhibited the increase in the level of all three leukocyte populations.

Red Blood Cell System.

In the assessment of red blood cell parameters, there was a decrease in the concentration of hemoglobin in erythrocytes (MCH and MCHC) in the group of rats with induced atopic dermatitis and treated with 1% hydrocortisone composition [p<0.05]. However, this effect was not seen in the groups with induced atopic dermatitis and treated with both the urolithin A composition in the two concentrations used 0.2 and 1.0% and the control group exposed only to petrolatum. This shows that the decrease in hematocrit level in the first of the discussed groups was caused by direct action of hydrocortisone and was not the result of atopic dermatitis.

The group of rats treated with the 1% hydrocortisone composition was also characterized by a decrease in the RDW parameter level [p<0.05], which was not observed in the other research groups, and which consequently can be explained by the action of hydrocortisone.

The changes observed in hematocrit and RDW levels were within physiological values in rat. However, it should be noted that although the RDW-% and fl indices are not clinically significant, with concurrent decrease in hemoglobin concentration in erythrocytes and normal RBC values maintained, there may be a tendency to hypochromatic anaemia caused by the long-term effect of hydrocortisone.

As to the other values of erythrocytic system parameters, i.e. RBC, HGB and HCT, MCV, no changes caused by atopic inflammation and the effect of both hydrocortisone and urolithin were observed.

Platelet system.

In the assessment of platelets parameters it was found an increase in the number of thrombocytes (PLT–1×109) and thrombocrit (PCT %) in the group of rats with induced atopic dermatitis, with the increase being slightly higher and reaching significantly higher values compared to the negative control group [p<0.05] only in rats treated with 1% hydocortisone (PLT), and for PCT % parameter in rats treated with petrolatum [p<0.05] or 1% hydrocortisone [p<0.01].

Other parameters of the platelet system, i.e. MPV (fl) and PDW (fl) as well as PDWcv (%) did not change as a result of atopic dermatitis or treatment undertaken with hydrocortisone or urolithin.

The changes observed in thrombocyte count (PLT–1×$10^9$) and thrombocrit (PCT %) were within physiological values in rats.

Effect of Urolithin a on the Levels of S100A8/A9, IL-8, TNF-Alpha and IL-1beta Secreted by Neutrophils Isolated from Human Peripheral Blood.

In order to comparatively study the biological activity of urolithins and their derivatives, these compounds were obtained by chemical synthesis, and then their activity against release of calprotectin by stimulated neutrophils was examined. Peripheral blood was collected from healthy donors (aged 20-35) at the Regional Blood Donation and Blood Treatment Center (Regionalne Centrum Krwiodawstwa i Krwiolecznictwa) in Warsaw. The study was conducted in accordance with the principles of the Declaration of Helsinki. Donors were non-smokers and did not take any medications. Neutrophils were isolated using a standard method (Piwowarski et al., 2014a). Neutrophils were then suspended in HBSS. 50 μL of urolithin A, urolithin B or iso-urolitin A at the appropriate concentration (to achieve final concentrations of 40, 10 and 1 μM) and 10 μL of LPS solution (final concentration of 10 ng/mL) were added to 440 μl of cell suspension (3×$10^5$ cells/mL). Cells were incubated at 37° C. for 30 min, then centrifuged at 4° C., 400 rcf for 10 min. The experiment was carried out on blood samples taken from 4 different donors in duplicates. The effect of urolithins on the production of S100A8/A9 was determined using the immunochemical ELISA method (R&D Systems).

After isolation, neutrophils were suspended in RPMI 1640 medium supplemented with L-glutamine, HEPES and 10% FBS and incubated with urolithin A and its acylated derivatives (SG1, SG2, SG3, SG4, SG1_m, SG2_m, SG3_m) at a concentration of 40 μM for 1 hour before stimulation with LPS from *Escherichia coli* (100 ng/mL). After 24 hours, IL-8, TNF-alpha and IL-1beta levels were determined using the immunochemical ELISA method (BD biosciences). The effect on neutrophil viability was assessed using annexin V and propidium iodide staining.

Results:

Urolithin A was the only among tested compounds belonging to the urolithin group incubated with human neutrophils that caused a significant decrease in the extracellular level of the S100A8/A9 protein (calprotectin). The activity shown was concentration dependent. It should also be emphasized that so far urolithin A is the only substance for which properties to lower the extracellular level of S100A8/A9 have been found.

Urolithin A showed inhibition of the production of proinflammatory cytokines, IL-8, TNF-alpha and IL-1beta, by human neutrophils. Attachment of the acyl group to the urolithin A molecule caused significant changes in its activity, with increased inhibition of the inflammatory response observed only for SG_1, SG1_m and SG2_m. Other derivatives either showed no effect or were enhancing neutrophil-mediated inflammatory response.

None of the compounds tested showed any influence on neutrophil viability.

The Effect of Urolithin a on the Viability of Human Fibroblasts In Vitro.

NHDF fibroblasts (human normal skin fibroblasts) were cultured in the DMEM medium supplemented with 10% FBS and a mixture of antibiotics—penicillin and streptomycin at 37° C., 5% $CO_2$. Cells were incubated with urolithin A, urolithin B, iso-urolithin A and acetylated urolithin derivatives A-SG1 and SG1_m as well as 3-acetyl-urolithin B at a concentration of 40 μM for 24 hours. After incubation with the compounds, the cells were washed twice with warm medium. The effect on cell viability was assessed using a standard MTT test.

Urolithin A, urolithin B, iso-urolithin A and acetylated derivatives of urolithin A-SG1 and SG1_mono did not affect the viability of human fibroblasts. 3-acetyl-urolithin B reduced cell viability by 27.4±10.4%.

The Effect of Urolithin a on the Production and Expression of Proinflammatory Cytokine TNF-Alpha and Phosphorylation of Protein Kinase ERK in a Model of Human Macrophages Obtained from Monocytes of the THP-1 Cell Line.

Monocytes of the THP-1 line were cultured in RPMI 1640 medium supplemented with 10% FBS and 2 mM glutamine. For transformation of monocytes into macrophages, the cells were treated with 12.5 ng/mL PMA (phorbol 12-myristate 13-acetate) for 48 hours, then washed and incubated for 24 hours in a culture medium without PMA. After this time, urolithin A, urolithin B, iso-urolithin A and the corresponding glucuronides (GUA, GUB and GiUA) were added to the cells at a concentration of 40 μM. After 1 hour of incubation with the compounds, the cells were stimulated with LPS from *Escherichia coli* (10 ng/mL).

To assess the level of TNF-alpha production, the cells were incubated for 6 hours, to assess the expression of mRNA for TNF-alpha, the cells were incubated for 24 hours, to assess the effect on ERK1/2 phosphorylation, the cells were incubated for 35 minutes.

The level of TNF-alpha in the culture medium was determined using the immunochemical ELISA method (BD biosciences). Evaluation of the expression of mRNA for TNF-alpha was performed using real time PCR. After 24 hours of incubation, RNA was isolated using NucleoSpin RNA Clean-up (Macherey-Nagel). The amount and quality of isolated RNA was determined using 2100 Bioanalyzer (Agilent Technologies). The expression level of mRNA for TNF-α was determined using Brilliant II SYBR Green QPCR Kit and Aria Mx Real-Time PCR thermocycler (Agilent Technologies). The following were used as primers for TNF-alpha: forward: 5'-GGCCTCTGTGCCTTCTTTTG-3', reverse: 5'-CCTCAGCAATGAGTGACAGT-3'. Beta-actin (ACTB) was used as the housekeeping gene; primer forward: 5'-TTGCCGACAGGATGCAGAAGGA-3', reverse: 5'-AGGTGGACAGCGAGGCCAGGAT-3').

ERK1/2 phosphorylation was assessed by Western blotting. After 35 minutes of stimulation with LPS, cell lysis was performed using cOmplete™ Lysis-M (Roche) containing a cocktail of protease inhibitors and phosphatases (Roche). Proteins were separated on a 12.5% SDS-PAGE gel and transferred to a nitrocellulose membrane. Subsequently, the membrane was incubated with rabbit primary antibodies: anti-ERK1/2 (Cell Signaling Technology), anti-p-ERK1/2, Thr202/Tyr204 (Cell Signaling Technology), anti-beta Actin (Abeam). The secondary antibody was HRP-conjugated goat anti-rabbit IgG antibody (Abeam). The membrane was developed using SignalFire ECL Reagent (Cell Signaling Technology) and visualized using the PXi 4 Touch (SYN-GENE) camera.

Urolithin A, urolithin B, iso-urolithin A and their corresponding glucuronides at a concentration of 40 μM were tested for effects on macrophage viability using a standard MTT test.

Results:

In the conducted studies of the inhibition of inflammatory response in a model of human macrophages obtained from monocytes of the THP-1 cell line, it was shown that inhibition of pro-inflammatory cytokine TNF-alpha production was characteristic only for urolithin A and its mono-acetylated SG1 and SG1_mono derivatives. Urolithin B and its acetylated derivative did not show any activity (FIG. 13). In parallel, studied iso-urolithin A with phenol groups in the 3- and 9-positions stimulated the production of TNF-alpha. GUA, GiUA and GUB glucuronide derivatives of urolithins did not show any activity. In addition, urolithin A has been shown to have an inhibitory effect on TNF-alpha mRNA expression, while urolithin B was inactive, and iso-urolithin A stimulated mRNA expression for this cytokine.

Studies of the MAPK signaling pathway have shown that the stimulation of ERK1/2 kinase phosphorylation by urolithin A is involved in the activity that inhibits TNF-alpha production. This activity was specific for urolithin A, since urolithin B did not exhibit such activity, while iso-urolithin A was much less active. Glucuronide derivatives were inactive.

The Effect of Urolithin a on the Production of Proinflammatory Cytokine TNF-Alpha in a Model of Human Macrophages Obtained from Monocytes Isolated from Human Peripheral Blood.

Monocytes were isolated from peripheral human blood by a standard method using dextran sedimentation and Ficoll Hypaque gradient centrifugation. After isolation, monocytes were suspended in RPMI 1640 medium supplemented with L-glutamine, HEPES, streptomycin, amphotericin and gentamicin, and 20% autologous serum. Cell culture was carried out under these conditions for 7 days. After this time, monocytes were transformed into macrophages and test compounds were added: urolithin A, urolithin B, iso-urolithin A and their corresponding glucuronides at a concentration of 40 μM and LPS from *Escherichia coli* (100 ng/mL). After 24h, TNF-alpha level in the medium was determined using the immunochemical ELISA method (BD biosciences).

Results:

Studies on macrophages isolated from human peripheral blood have confirmed that the most active compound in the inhibition of TNF-alpha production is urolithin A. As with the studies on the THP-1 cell line, urolithin B was inactive, and the urolithin A isomer—iso-urolithin A was significantly less active.

Based on the above results, it was found that the factor which conditions the inhibition of inflammatory response is the presence of two phenol groups located in strictly defined positions 3- and 8-of urolithin A molecule. These groups can be esterified with acetyl residues, which can lead to increasing anti-inflammatory activity, while attachment of glucuronic acid residues or other acyl groups causes loss of anti-inflammatory activity.

The obtained results of experiments on in vitro models were analyzed using the Statistica 13 program (StatSoft, Inc., Tulsa, OK, USA) and presented as mean values±SEM. Statistical significance was set at P≤0.05. The results with established normal distribution in the D'Agostin and Pearson test were prepared using analysis of variance (ANOVA). Parametric post-hoc analysis was performed using Dunnett's test.

The Effect of Local Therapy Using Urolithin a on Inflammatory Changes Caused by Inflammatory Skin Diseases, in Particular Atopic Dermatitis and Psoriasis.

The therapeutic composition was an ointment prepared on the base of white petrolatum with 1.0% urolithin A added. The control ointment was white petrolatum without the addition of urolithin A. 1.0% urolithin A composition and the carrier—white petrolatum was applied on washed and dried skin by volunteers themselves, at a dose of 20 mg ointment per surface 4 cm$^2$ daily, once a day for two weeks.

The following parameters were taken into account in the study: feeling of discomfort after application of the composition on the skin, ease of application, discoloration of the skin at the site of application, redness of the skin at the site of application of the composition, degree of drying of the treated area of the skin, sensation of pinching, burning, itching and other types of discomfort. Participants in the study determined their level of satisfaction/dissatisfaction on a 10-point scale, 0 being dissatisfaction and 10 being satisfaction with the pharmaceutical composition of the present invention. It has been demonstrated that the use of a composition containing urolithin A did not cause any adverse effects, unlike the adverse reactions following the use of hydrocortisone.

Thermal Stability of Urolithin a in Water and in an Acidic Environment.

Urolithin A at 80 μM was suspended in deionized water or 1M HCl and incubated for 24 hours at 37° C. or for 12 hours at 80° C. The urolithin A solution was also irradiated for 12 hours with a UV lamp emitting UVA radiation with the maximum at 365 nm. The concentration of urolithin A after incubation was determined using the UPLC-DAD-MS method according to Piwowarski et al. 2016.

Results:

Urolithin A was stable under the conditions studied—no degradation of urolithin A nor any change in the chemical structure of the compound were observed.

Since skin preparations contain large amounts of water and the skin pH is 5.5, the stability of urolithin A in the aquatic environment and at low pH is particularly important for the development of skin preparations which contain it. Stability under the influence of UV radiation is of importance when storing the preparation and sun exposure the preparation applied to the skin.

Non-Patent Literature

D'Amico, F., Granata, M., Skarmoutsou, E., Trovato, C., Lovero, G., Gangemi, P., Longo, V., Pettinato, M., Mazzarino, M. C., 2018. Biological therapy downregulates the heterodimer S100A8/A9 (calprotectin) expression in psoriatic patients. Inflamm Res 67, 609-616.

Furue, K., Ito, T., Tsuji, G., Kadono, T., Nakahara, T., Furue, M., 2018. Autoimmunity and autoimmune co-morbidities in psoriasis. Immunology 154, 21-27.

Liu, C. F., Li, X. L., Zhang, Z. L., Qiu, L., Ding, S. X., Xue, J. X., Zhao, G. P., Li, J., 2018. Anti-aging Effects Of Urolithin A On Replicative Senescent Human Skin Fibroblasts. Rejuvenation Res 22, 191-200.

Papier, A., Strowd, L. C., 2018. Atopic dermatitis: a review of topical nonsteroid therapy. Drugs Context 7, 212521.

Tomas-Barberan, F. A., Selma, M. V., Espin, J. C., 2018. Polyphenols' Gut Microbiota Metabolites: Bioactives or Biomarkers? Journal of Agricultural and Food Chemistry 66, 3593-3594.

Yadav, K., Singh, D., Singh, M. R., 2018. Protein biomarker for psoriasis: A systematic review on their role in the pathomechanism, diagnosis, potential targets and treatment of psoriasis. Int J Biol Macromol 118, 1796-1810.

Pastore, S., Mascia, F., Mariotti, F., Dattilo, C., Mariani, V., Girolomoni, G., 2005. ERK1/2 Regulates Epidermal Chemokine Expression and Skin Inflammation. J Immunol 174, 5047-505.

Tomas-Barberan, F. A., Gonzalez-Sarrias, A., Garcia-Villalba, R., Nunez-Sanchez, M. A., Selma, M. V., Garcia-Conesa, M. T., Espin, J. C., 2017. Urolithins, the rescue of "old" metabolites to understand a "new" concept: Metabotypes as a nexus among phenolic metabolism, microbiota dysbiosis, and host health status. Mol Nutr Food Res 61, 1500901.

Deng, Y., Chang, C., Lu, Q., 2016. The Inflammatory Response in Psoriasis: a Comprehensive Review. Clin Rev Allergy Immunol 50, 377-389.

Eichenfield, L. F. M., Friedlander, S. F. M., Simpson, E. L. M. M., Irvine, A. D. M., 2016. Assessing the New and Emerging Treatments for Atopic Dermatitis. Semin Cutan Med Surg 35, S92-96.

Piwowarski, J. P., Granica, S., Stefanska, J., Kiss, A. K., 2016. Differences in Metabolism of Ellagitannins by Human Gut Microbiota ex Vivo Cultures. J Nat Prod 79, 3022-3030.

Pruenster, M., Vogl, T., Roth, J., Sperandio, M., 2016. S100A8/A9: From basic science to clinical application. Pharmacol Ther 167,120-131.

Weidinger, S., Novak, N., 2016. Atopic dermatitis. Lancet 387, 1109-1122.

D'Haens, G., Sandborn, W. J., Colombel, J. F., Rutgeerts, P., Brown, K., Barkay, H., Sakov, A., Haviv, A., Feagan, B.

G., Laquinimod for Crohn's Disease, I., 2015. A phase II study of laquinimod in Crohn's disease. Gut 64, 1227-1235.

Piwowarski, J. P., Kiss, A. K., 2015. Contribution of C-glucosidic ellagitannins to *Lythrum salicaria* L. influence on pro-inflammatory functions of human neutrophils. J Nat Med 69, 100-110.

Piwowarski, J. P., Kiss, A. K., Granica, S., Moeslinger, T., 2015. Urolithins, gut microbiota-derived metabolites of ellagitannins, inhibit LPS-induced inflammation in RAW 264.7 murine macrophages. Mol Nutr Food Res 59, 2168-2177.

Tuohy, K., Del Rio, D., 2015. Diet-Microbe Interactions in the Gut. Effects on Human Health and Disease. Elsevier.

Jin, S., Park, C. O., Shin, J. U., Noh, J. Y., Lee, Y. S., Lee, N. R., Kim, H. R., Noh, S., Lee, Y., Lee, J. H., Lee, K. H., 2014. DAMP molecules S100A9 and S100A8 activated by IL-17A and house-dust mites are increased in atopic dermatitis. Exp Dermatol 23, 938-941.

Piwowarski, J. P., Granica, S., Kiss, A. K., 2014a. Influence of gut microbiota-derived ellagitannins' metabolites urolithins on pro-inflammatory activities of human neutrophils. Planta Med 80, 887-895.

Piwowarski, J. P., Granica, S., Zwierzynska, M., Stefanska, J., Schopohl, P., Melzig, M. F., Kiss, A. K., 2014b. Role of human gut microbiota metabolism in the anti-inflammatory effect of traditionally used ellagitannin-rich plant materials. J Ethnopharmacol 155, 801-809.

Colombo, E., Sangiovanni, E., Dell'agli, M., 2013. A review on the anti-inflammatory activity of pomegranate in the gastrointestinal tract. Evidence-based complementary and alternative medicine: eCAM 2013, 247145.

D'Orazio, J., Jarrett, S., Amaro-Ortiz, A., Scott, T., 2013. UV radiation and the skin. Int J Mol Sci 14, 12222-12248.

Espin, J. C., Larrosa, M., Garcia-Conesa, M. T., Tomas-Barberan, F., 2013. Biological significance of urolithins, the gut microbial ellagic Acid-derived metabolites: the evidence so far. Evidence-based complementary and alternative medicine: eCAM 2013, 270418.

Haiser, H. J., Turnbaugh, P. J., 2013. Developing a metagenomic view of xenobiotic metabolism. Pharmacological research 69, 21-31.

Schonthaler, H. B., Guinea-Viniegra, J., Wculek, S. K., Ruppen, I., Ximenez-Embun, P., Guio-Carrion, A., Navarro, R., Hogg, N., Ashman, K., Wagner, E. F., 2013. S100A8-S100A9 protein complex mediates psoriasis by regulating the expression of complement factor C3. Immunity 39, 1171-1181.

Bengtsson, A. A., Sturfelt, G., Lood, C., Ronnblom, L., van Vollenhoven, R. F., Axelsson, B., Sparre, B., Tuvesson, H., Ohman, M. W., Leanderson, T., 2012. Pharmacokinetics, tolerability, and preliminary efficacy of paquinimod (ABR-215757), a new quinoline-3-carboxamide derivative: studies in lupus-prone mice and a multicenter, randomized, double-blind, placebo-controlled, repeat-dose, dose-ranging study in patients with systemic lupus erythematosus. Arthritis Rheum 64, 1579-1588.

Comi, G., Jeffery, D., Kappos, L., Montalban, X., Boyko, A., Rocca, M. A., Filippi, M., Group, A. S., 2012. Placebo-controlled trial of oral laquinimod for multiple sclerosis. N Engl J Med 366, 1000-1009.

Ishimoto, H., Shibata, M., Myojin, Y., Ito, H., Sugimoto, Y., Tai, A., Hatano, T., 2011. In vivo anti-inflammatory and antioxidant properties of ellagitannin metabolite urolithin A. Bioorg Med Chem Lett 21, 5901-5904.

Larrosa, M., Garcia-Conesa, M. T., Espin, J. C., Tomas-Barberan, F. A., 2010a. Ellagitannins, ellagic acid and vascular health. Molecular aspects of medicine 31, 513-539.

Larrosa, M., Gonzalez-Sarrias, A., Yanez-Gascon, M. J., Selma, M. V., Azorin-Ortuno, M., Toti, S., Tomas-Barberan, F., Dolara, P., Espin, J. C., 2010b. Anti-inflammatory properties of a pomegranate extract and its metabolite urolithin-A in a colitis rat model and the effect of colon inflammation on phenolic metabolism. J Nutr Biochem 21, 717-725.

Bialonska, D., Kasimsetty, S. G., Khan, S. I., Ferreira, D., 2009. Urolithins, intestinal microbial metabolites of Pomegranate ellagitannins, exhibit potent antioxidant activity in a cell-based assay. J Agric Food Chem 57, 10181-10186.

Bjork, P., Bjork, A., Vogl, T., Stenstrom, M., Liberg, D., Olsson, A., Roth, J., Ivars, F., Leanderson, T., 2009. Identification of human S100A9 as a novel target for treatment of autoimmune disease via binding to quinoline-3-carboxamides. PLoS Biol 7, e97.

Odhiambo, J. A., Williams, H. C., Clayton, T. O., Robertson, C. F., Asher, M. I., Group, I. P. T. S., 2009. Global variations in prevalence of eczema symptoms in children from ISAAC Phase Three. J Allergy Clin Immunol 124, 1251-1258 e1223.

Breneman, D., Fleischer, A. B., Jr., Abramovits, W., Zeichner, J., Gold, M. H., Kirsner, R. S., Shull, T. F., Crowe, A. W., Jaracz, E., Hanifin, J. M., Tacrolimus Ointment Study, G., 2008. Intermittent therapy for flare prevention and long-term disease control in stabilized atopic dermatitis: a randomized comparison of 3-times-weekly applications of tacrolimus ointment versus vehicle. J Am Acad Dermatol 58, 990-999.

Berth-Jones, J., Damstra, R. J., Golsch, S., Livden, J. K., Van Hooteghem, O., Allegra, F., Parker, C. A., Multinational Study, G., 2003. Twice weekly fluticasone propionate added to emollient maintenance treatment to reduce risk of relapse in atopic dermatitis: randomised, double blind, parallel group study. BMJ 326, 1367.

The invention claimed is:

1. A method for the treatment or inhibition of inflammation caused by an inflammatory condition of skin and/or mucous membranes, comprising administering to a patient in need thereof a pharmaceutical composition which comprises one or more typical auxiliary substances and an active ingredient which is urolithin A or urolithin A 3,8-diacetate, wherein the pharmaceutical composition is administered by external topical administration.

2. The method of claim 1, wherein urolithin A is synthetic urolithin A.

3. The method of claim 1, wherein said active ingredient is present in the amount from about 0.0001 weight percent to about 15 weight percent based on the total weight of the composition.

4. The method of claim 1, further comprises at least one drug selected from the group consisting of steroids, calcineurin inhibitors, and drugs with antibacterial, antifungal or antiviral activity.

5. The method of claim 1, wherein urolithin A is the only active ingredient present in the composition.

6. The method of claim 1, wherein said at least one pharmaceutically acceptable auxiliary substance is selected from a carrier and/or an excipient and/or a diluent and combinations thereof.

7. The method of claim 1, wherein said pharmaceutically acceptable auxiliary substance is one or more of protective agents, adsorbents, demulcents, emollients, preservatives, antioxidants, moisturizers, buffering agents and solubilizing agents.

8. The method of claim 1, wherein the composition is administered to an inflamed area in an amount in the range from about 0.0001 g/cm$^2$ of skin surface area to about 0.5 g/cm$^2$ of skin surface area.

9. The method of claim 1, wherein said pharmaceutical composition is in a liquid form.

10. The method of claim 1, wherein said pharmaceutical composition is in a semi-solid form.

11. The method of claim 9, wherein said pharmaceutical composition is administered to the inflamed area manually.

12. The method of claim 1, wherein said pharmaceutical composition is in the form of a transdermal therapeutic system.

13. The method of claim 1, wherein said inflammatory condition of the skin and/or the mucous membranes is psoriasis.

14. The method of claim 1, wherein said inflammatory condition of the skin and/or the mucous membranes is atopic dermatitis.

15. The method of claim 1, wherein the inflammatory condition of the skin and/or the mucous membranes is selected from the group consisting of skin inflammations, vasculitides, lupus erythematosus, dermatomyositis, scleroderma, multiple sclerosis, giant cell arteritis, psoriasis, atopic dermatitis, seborrheic dermatitis, contact dermatitis, urticaria, rosacea, dermatitis herpetiformis, lichen planus, hidradenitis suppurativa, pityriasis rosea of Gibert, hydrocystoma, aphthae, diaper dermatitis, adolescent acne, non-allergic contact eczema, panniculitis, and cellulitis.

16. The method of claim 9, wherein the liquid form is in the form of a tonic, balm, lotion, foam.

17. The method of claim 10, wherein the semi-solid form is in the form of an ointment, cream, paste, gel.

18. The method of claim 11, wherein said pharmaceutical composition is administered to the inflamed area manually using a dropper, application stick or spray applicator.

19. The method of claim 12, wherein the transdermal therapeutic system is in the form of an intradermal patch or a transdermal patch.

* * * * *